(12) United States Patent
Bansal

(10) Patent No.: US 8,664,362 B2
(45) Date of Patent: Mar. 4, 2014

(54) HUMANIZED AND CHIMERIC ANTI-PROPERDIN ANTIBODIES

(75) Inventor: Rekha Bansal, Twinsburg, OH (US)

(73) Assignee: Novelmed Therapeutics, Cleveland, OH (US)

( * ) Notice: Subject to any disclaimer, the term of this patent is extended or adjusted under 35 U.S.C. 154(b) by 0 days.

(21) Appl. No.: 13/583,879

(22) PCT Filed: Mar. 10, 2011

(86) PCT No.: PCT/US2011/027964
§ 371 (c)(1),
(2), (4) Date: Sep. 10, 2012

(87) PCT Pub. No.: WO2011/112850
PCT Pub. Date: Sep. 15, 2011

(65) Prior Publication Data
US 2013/0004485 A1    Jan. 3, 2013

Related U.S. Application Data

(60) Provisional application No. 61/312,469, filed on Mar. 10, 2010.

(51) Int. Cl.
*C07K 16/00* (2006.01)
*C12P 21/08* (2006.01)
*A61K 39/395* (2006.01)
*A61K 39/00* (2006.01)

(52) U.S. Cl.
USPC ............. 530/387.1; 530/387.3; 530/387.9; 424/130.1; 424/133.1

(58) Field of Classification Search
None
See application file for complete search history.

(56) References Cited

U.S. PATENT DOCUMENTS

| 2003/0198636 A1 | 10/2003 | Gupta-Bansal et al. |
| 2006/0093599 A1 | 5/2006 | Gazit-Bornstein et al. |
| 2010/0021416 A1 | 1/2010 | Lichter et al. |

FOREIGN PATENT DOCUMENTS

WO    WO-2008-154018 A2    12/2008

OTHER PUBLICATIONS

Gupta-Bansal, R., et al., "Inhibition of complement alternative pathway function with anti-perperdin monoclonal antibodies", Molecular Immunology, Apr. 2000, vol. 37, Issue 5.

*Primary Examiner* — Daniel E Kolker
*Assistant Examiner* — James Rogers
(74) *Attorney, Agent, or Firm* — Tarolli, Sundheim, Covell & Tummino LLP

(57) ABSTRACT

An isolated anti-properdin antibody or antigen binding portion thereof includes a heavy chain variable domain including the 3CDRs in SEQ ID NO: 1 and light chain variable domain including the 3 CDRS in SEQ ID NO: 9.

8 Claims, 29 Drawing Sheets

Anti-Properdin Antibody Does Not Inhibit Classical Pathway

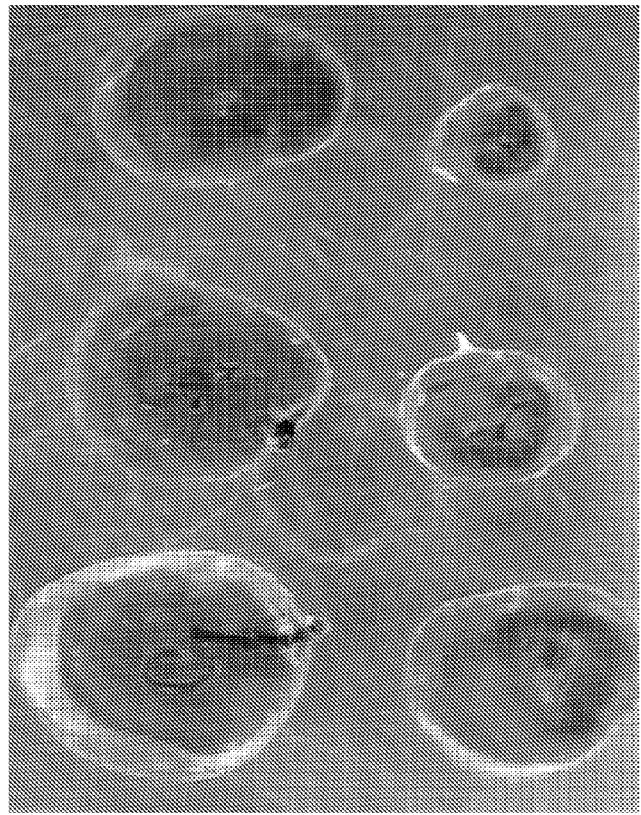
Treated Rabbit Heart
Fig. 13
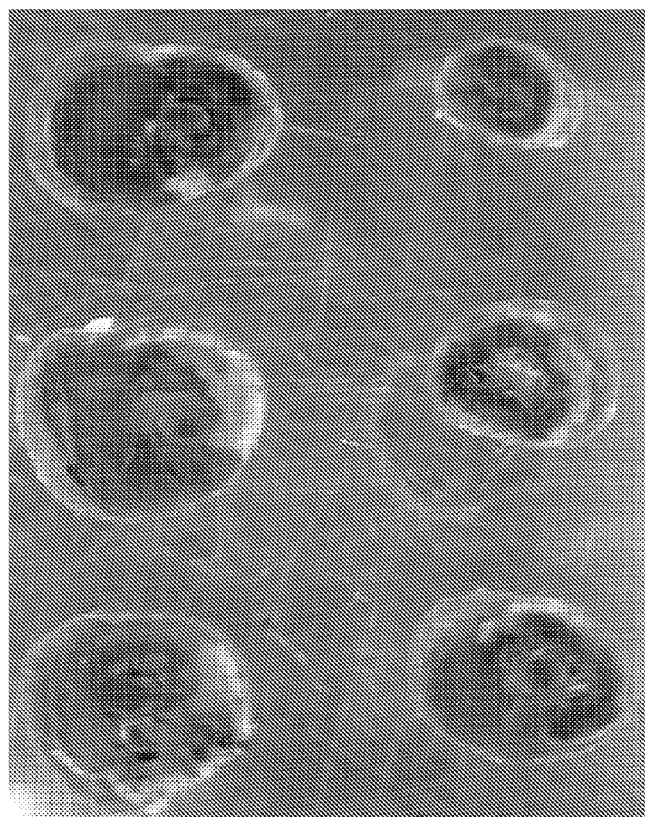
Control Rabbit Heart

Anti-Properdin Inhibits Choroidal NeoVascularization

Anti-Properdin Inhibits Rheumatoid Arthritis

SEQ ID NO 1: Variable Region of Heavy Chain
QVQLQQSAPELARPGASVKMSCTASGYIFTNYPIHWVK
QRPGQGLEWIGFIDPGGGYDEPDERFRDRATLTADKSS
STAYMQLSSLTSEDSAIYYCARRGGGYYLDYWGQGTTLT
VSSAKTT SEQ ID NO 2: Heavy Chain Frame Work #1
QVQLQQSAPELARPGASVKMSCTAS SEQ ID NO 3: Heavy Chain Frame Work #2
WVKQRPGQGLEWIG SEQ ID NO 4: Heavy chain Framework #3
RATLTADKSSSTAYMQLSSLTSEDSAIYYCAR SEQ ID NO 5: Heavy Chain Frame Work #4
WGQGTTLTVSSAKTT SEQ ID NO 6: Heavy Chain CDR-H1
GYIFTNYPIH SEQ ID NO 7: Heavy Chain CDR-H2
FIDPGGGYDEPDERFRD SEQ ID NO 8: Heavy Chain CDR-H3
RGGGYYLDY

Fig. 16

SEQ ID NO 9: Variable Region of the Light Chain
DIQMTQTTSSLSASLGDRVTISCRASQDISFFLNWYQQ
KPDGTVKLLIYTSRYHSGVPSRFSGSGSGTDFSLTIN
NLEQEDFATYFCQHGNTLPWTFGGGTKLEIKRADAAPT
VSIFPPSSEQLTSGGASVVCFLNN SEQ ID NO 10: Light Chain Frame Work #1
DIQMTQTTSSLSASLGDRVTISC SEQ ID NO 11: Light Chain Frame Work #2
WYQQKPDGTVKLLIY SEQ ID NO 12: Light chain Framework #3
GVPSRFSGSGSGTDFSLTINNLEQEDFATYF SEQ ID NO 13: Light Chain Framework #4
FGGGTKLEIKRADAAPTVSIFPPSSEQLTSGGASVVCFL
NN SEQ ID NO 14: Light Chain CDR-L1
RASQDISFFLN SEQ ID NO 15: Light Chain CDR-L2
YTSRYHS SEQ ID NO 16: Light Chain CDR-L3
QHGNTLPWT

Fig. 17

Chimeric and Humanized Antibodies – Light Chain Sequences

Chimeric

SEQ ID NO 17
>BAP010_1LC
DIQMTQTTSSLSASLGDRVTISCRASQDISFFLNWYQQKPDGTVKLLIYYTSRYHSGVPSRFSGSGSGT
DFSLTINNLEQEDFATYFCQHGNTLPWTFGGG

Humanized

SEQ ID NO 18
>BAP010hum01_LC
DIQMTQSPSSLSASVGDRVTITCRASQDISFFLNWYQQKPGKAPKLLIYYTSRYHSGVPSRFSGSGSGT
EFTLTISSLQSEDFAVYYCQHGNTLPWTFGQG SEQ ID NO 19
>BAP010hum02_LC
EIVLTQSPATLSLSPGERATLSCRASQDISFFLNWFQQRPGQSPRRLIYYTSRYHSGIPPRFSGSGYGTD
FTLTINNIESEDAAYYFCQHGNTLPWTFGQG SEQ ID NO 20
>BAP010hum03_LC
DIQMTQSPSSLSASVGDRVTITCRASQDISFFLNWYQQKPGKAPKLLIYYTSRYHSGVPSRFSGSGSGT
EFTLTISSLQSEDFAVYYCQHGNTLPWTFGQG SEQ ID NO 21
>BAP010hum04_LC
DIQMTQSPSSLSASVGDRVTITCRASQDISFFLNWYLQKPGQSPQLLIYYTSRYHSGVPSRFSGSGSGT
EFTLTISSLQPDDFATYYCQHGNTLPWTFGQG

Fig. 21

Humanized Antibodies – Light Chain Sequences

SEQ ID NO 22
>BAP010hum05_LC
EIVMTQSPATLSVSPGERATLSCRASQDISFFLNWYQQKPGKAPKLLIYYTSRYHSGVPSRFSGSG
SGTDFTFTISSLQPEDIATYYCQHGNTLPWTFGQG SEQ ID NO 23
>BAP010hum06_LC
EIVMTQSPATLSVSPGERATLSCRASQDISFFLNWYQQKPGKAPKLLIYYTSRYHSGVPSRFSGSG
SGTDFTFTISSLQPEDIATYYCQHGNTLPWTFGQG SEQ ID NO 24
>BAP010hum07_LC
EIVMTQSPATLSVSPGERATLSCRASQDISFFLNWYQQKPGKAPKLLIYYTSRYHSGVPSRFSGSG
SGTDFTFTISSLQPEDIATYYCQHGNTLPWTFGQG SEQ ID NO 25
>BAP010hum08_LC
DIQMTQSPSSLSASVGDRVTITCRASQDISFFLNWYLQKPGQSPQLLIYYTSRYHSGVPSRFSGSG
SGTEFTLTISSLQPDDFATYYCQHGNTLPWTFGQG SEQ ID NO 26
>BAP010hum09_LC
DIQMTQSPSSLSASVGDRVTITCRASQDISFFLNWYQQKPGKAPKLLIYYTSRYHSGVPSRFSGSG
SGTEFTLTISSLQSEDFAVYYCQHGNTLPWTFGQG SEQ ID NO 27
>BAP010hum10_LC
DIQMTQSPSSLSASVGDRVTITCRASQDISFFLNWYQQKPGKAPKLLIYYTSRYHSGIPPRFSGSG
YGTEFTFTISSLEAEDAATYYCQHGNTLPWTFGQG

Fig. 22

Chimeric and Humanized Antibodies – Light Chain Sequences

SEQ ID NO 28
>BAP010hum11_LC
DIQMTQSPSSLSASVGDRVTITCRASQDISFFLNWYQQKPGKAPKLLIYYTSRYHSGVPSRFSGS
GSGTEFTLTISSLQSEDFAVYYCQHGNTLPWTFGQG SEQ ID NO 29
>BAP010hum12_LC
DIQMTQSPSSLSASVGDRVTITCRASQDISFFLNWYLQKPGQSPQLLIYYTSRYHSGVPSRFSGS
GSGTEFTLTISSLQPDDFATYYCQHGNTLPWTFGQG SEQ ID NO 30
>BAP010hum13_LC
DIQMTQSPSSLSASVGDRVTITCRASQDISFFLNWYQQKPGKAPKLLIYYTSRYHSGVPSRFSGS
GSGTEFTLTISSLQSEDFAVYYCQHGNTLPWTFGQG SEQ ID NO 31
>BAP010hum14_LC
DIQMTQSPSSLSASVGDRVTITCRASQDISFFLNWYQQKPGKAPKLLIYYTSRYHSGIPPRFSGS
GYGTEFTFTISSLEAEDAATYYCQHGNTLPWTFGQG SEQ ID NO 32
>BAP010hum15_LC
EIVMTQSPATLSVSPGERATLSCRASQDISFFLNWYQQKPGKAPKLLIYYTSRYHSGVPSRFSGS
GSGTDFTFTISSLQPEDIATYYCQHGNTLPWTFGQG SEQ ID NO 33
>BAP010hum16_LC
DIQMTQSPSSLSASVGDRVTITCRASQDISFFLNWYQQKPGKAPKLLIYYTSRYHSGVPSRFSGS
GSGTEFTLTISSLQSEDFAVYYCQHGNTLPWTFGQG

Fig. 23

Chimeric and Humanized Antibodies – Heavy Chain Sequences

Chimeric
SEQ ID NO 34
>BAP010_1HC
QVQLQQSAPELARPGASVKMSCTASGYIFTNYPIHWVKQRPGQGLEWIGFIDPGGGYDEPDERFRDR
ATLTADKSSSTAYMQLSSLTSEDSAIYYCARRGGGYYLDYWGQG

Humanized
SEQ ID NO 35
>BAP010hum01_HC
QVQLQESGPGLVKPSQTLSLTCTVSGYIFTNYPIHWVRQAPGKGLEWVSFIDPGGGYDEPDERFRDRV
TISVDTSKNQFSLKLSSVTAADTAVYYCARRGGGYYLDYWGQG SEQ ID NO 36
>BAP010hum02_HC
EVQLVQSGAEVKKPGESLRISCKGSGYIFTNYPIHWIRQPPGKGLEWIGFIDPGGGYDEPDERFRDRFV
FSLDTSVSTAYLQICSLKAEDTAVYYCARRGGGYYLDYWGQG SEQ ID NO 37
>BAP010hum03_HC
EVQLVQSGAEVKKPGESLRISCKGSGYIFTNYPIHWIRQSPSRGLEWLGFIDPGGGYDEPDERFRDRV
TISADKSISTAYLQWSSLKASDTAMYYCARRGGGYYLDYWGQG SEQ ID NO 38
>BAP010hum04_HC
QVQLQESGPGLVKPSQTLSLTCTVSGYIFTNYPIHWVRQAPGKGLEWVSFIDPGGGYDEPDERFRDRV
TISVDTSKNQFSLKLSSVTAADTAVYYCARRGGGYYLDYWGQG SEQ ID NO 39
>BAP010hum05_HC
QVQLQESGPGLVKPSQTLSLTCTVSGYIFTNYPIHWVRQAPGKGLEWVSFIDPGGGYDEPDERFRDRV
TISVDTSKNQFSLKLSSVTAADTAVYYCARRGGGYYLDYWGQG

Fig. 24

Chimeric and Humanized Antibodies – Heavy Chain Sequences

SEQ ID NO 40
>BAP010hum06_HC
EVQLVQSGAEVKKPGESLRISCKGSGYIFTNYPIHWIRQPPGKGLEWIGFIDPGGGYDEPDERFRDRFVFS
LDTSVSTAYLQICSLKAEDTAVYYCARRGGGYYLDYWGQG SEQ ID NO 41
>BAP010hum07_HC
EVQLVQSGAEVKKPGESLRISCKGSGYIFTNYPIHWVRQAPGQGLEWMGFIDPGGGYDEPDERFRDRFV
FSLDTSVSTAYLQICSLKAEDTAVYYCARRGGGYYLDYWGQG SEQ ID NO 42
>BAP010hum08_HC
EVQLVQSGAEVKKPGESLRISCKGSGYIFTNYPIHWIRQPPGKGLEWIGFIDPGGGYDEPDERFRDRFVFS
LDTSVSTAYLQICSLKAEDTAVYYCARRGGGYYLDYWGQG SEQ ID NO 43
>BAP010hum09_HC
EVQLVQSGAEVKKPGESLRISCKGSGYIFTNYPIHWIRQPPGKGLEWIGFIDPGGGYDEPDERFRDRFVFS
LDTSVSTAYLQICSLKAEDTAVYYCARRGGGYYLDYWGQG SEQ ID NO 44
>BAP010hum10_HC
QVQLQESGPGLVKPSQTLSLTCTVSGYIFTNYPIHWVRQATGQGLEWMGFIDPGGGYDEPDERFRDRVTI
TADKSTSTAYMELSSLRSEDTAVYYCARRGGGYYLDYWGQG SEQ ID NO 45
>BAP010hum11_HC
EVQLVQSGAEVKKPGESLRISCKGSGYIFTNYPIHWVRQAPGKGLEWVSFIDPGGGYDEPDERFRDRLTIS
KDTSKNQVVLTMTNMDPVDTATYYCARRGGGYYLDYWGQG

Fig. 25

Chimeric and Humanized Antibodies – Heavy Chain Sequences

SEQ ID NO 46
>BAP010hum12_HC
EVQLVQSGAEVKKPGATVKISCKVSGYIFTNYPIHWVRQAPGKGLEWVSFIDPGGGYDEPDERFRDRFTISRD
NAKNSLYLQMNSLRAEDTAVYYCARRGGGYYLDYWGQG SEQ ID NO 47
>BAP010hum13_HC
EVQLVQSGAEVKKPGATVKISCKVSGYIFTNYPIHWVRQAPGKGLEWVSFIDPGGGYDEPDERFRDRFTISRD
NAKNSLYLQMNSLRAEDTAVYYCARRGGGYYLDYWGQG SEQ ID NO 48
>BAP010hum14_HC
EVQLVQSGAEVKKPGESLRISCKGSGYIFTNYPIHWVRQAPGKGLEWVSFIDPGGGYDEPDERFRDRVTISVD
TSKNQFSLKLSSVTAADTAVYYCARRGGGYYLDYWGQG SEQ ID NO 49
>BAP010hum15_HC
EVQLVQSGAEVKKPGATVKISCKVSGYIFTNYPIHWVRQAPGKGLEWVSFIDPGGGYDEPDERFRDRFTISRD
NAKNSLYLQMNSLRAEDTAVYYCARRGGGYYLDYWGQG SEQ ID NO 50
>BAP010hum16_HC
EVQLVQSGAEVKKPGESLRISCKGSGYIFTNYPIHWVRQATGQGLEWMGFIDPGGGYDEPDERFRDRFTISR
DDSKNTAYLQMNSLKTEDTAVYYCTRRGGGYYLDYWGQG

Fig. 26

EPITOPE MAPPING FOR ANTI-PROPERDIN ANTIBODY BINDING TO HUMAN PROPERDIN

SEQ ID 51: SPRWSLWSTWAPCSVTCSEGSQLRYRRCVGWNG

SEQUENCE LISTING

<160> NUMBER OF SEQ ID NOS: 51

<210> SEQ ID NO 1
<211> LENGTH: 122
<212> TYPE: PRT
<213> ORGANISM: Mus musculus

<400> SEQUENCE: 1

Gln Val Gln Leu Gln Gln Ser Ala Pro Glu Leu Ala Arg Pro Gly Ala
1               5                   10                  15

Ser Val Lys Met Ser Cys Thr Ala Ser Gly Tyr Ile Phe Thr Asn Tyr
            20                  25                  30

Pro Ile His Trp Val Lys Gln Arg Pro Gly Gln Gly Leu Glu Trp Ile
        35                  40                  45

Gly Phe Ile Asp Pro Gly Gly Gly Tyr Asp Glu Pro Asp Glu Arg Phe
    50                  55                  60

Arg Asp Arg Ala Thr Leu Thr Ala Asp Lys Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Arg Gly Gly Gly Tyr Tyr Leu Asp Tyr Trp Gly Gln Gly Thr
            100                 105                 110

Thr Leu Thr Val Ser Ser Ala Lys Thr Thr
        115                 120

<210> SEQ ID NO 2
<211> LENGTH: 25
<212> TYPE: PRT
<213> ORGANISM: Homo sapiens

<400> SEQUENCE: 2

Gln Val Gln Leu Gln Gln Ser Ala Pro Glu Leu Ala Arg Pro Gly Ala
1               5                   10                  15

Ser Val Lys Met Ser Cys Thr Ala Ser
            20                  25

<210> SEQ ID NO 3
<211> LENGTH: 14

```
<212> TYPE: PRT
<213> ORGANISM: Homo sapiens

<400> SEQUENCE: 3

Trp Val Lys Gln Arg Pro Gly Gln Gly Leu Glu Trp Ile Gly
1               5                   10

<210> SEQ ID NO 4
<211> LENGTH: 32
<212> TYPE: PRT
<213> ORGANISM: Homo sapiens

<400> SEQUENCE: 4

Arg Ala Thr Leu Thr Ala Asp Lys Ser Ser Ser Thr Ala Tyr Met Gln
1               5                   10                  15

Leu Ser Ser Leu Thr Ser Glu Asp Ser Ala Ile Tyr Tyr Cys Ala Arg
            20                  25                  30

<210> SEQ ID NO 5
<211> LENGTH: 15
<212> TYPE: PRT
<213> ORGANISM: Homo sapiens

<400> SEQUENCE: 5

Trp Gly Gln Gly Thr Thr Leu Thr Val Ser Ser Ala Lys Thr Thr
1               5                   10                  15

<210> SEQ ID NO 6
<211> LENGTH: 10
<212> TYPE: PRT
<213> ORGANISM: Homo sapiens

<400> SEQUENCE: 6

Gly Tyr Ile Phe Thr Asn Tyr Pro Ile His
1               5                   10

<210> SEQ ID NO 7
<211> LENGTH: 17
<212> TYPE: PRT
<213> ORGANISM: Homo sapiens

<400> SEQUENCE: 7

Phe Ile Asp Pro Gly Gly Gly Tyr Asp Glu Pro Asp Glu Arg Phe Arg
1               5                   10                  15

Asp

<210> SEQ ID NO 8
<211> LENGTH: 9
<212> TYPE: PRT
<213> ORGANISM: Homo sapiens

<400> SEQUENCE: 8

Arg Gly Gly Gly Tyr Tyr Leu Asp Tyr
1               5

<210> SEQ ID NO 9
<211> LENGTH: 138
<212> TYPE: PRT
<213> ORGANISM: Homo sapiens

<400> SEQUENCE: 9

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Phe Phe
```

-continued

```
                    20                  25                  30
Leu Asn Trp Tyr Gln Gln Lys Pro Asp Gly Thr Val Lys Leu Leu Ile
            35                  40                  45

Tyr Tyr Thr Ser Arg Tyr His Ser Gly Val Pro Ser Arg Phe Ser Gly
        50                  55                  60

Ser Gly Ser Gly Thr Asp Phe Ser Leu Thr Ile Asn Asn Leu Glu Gln
65                  70                  75                  80

Glu Asp Phe Ala Thr Tyr Phe Cys Gln His Gly Asn Thr Leu Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Glu Gln Leu Thr Ser Gly
        115                 120                 125

Gly Ala Ser Val Val Cys Phe Leu Asn Asn
        130                 135
```

<210> SEQ ID NO 10
<211> LENGTH: 23
<212> TYPE: PRT
<213> ORGANISM: Homo sapiens

<400> SEQUENCE: 10

```
Asp Ile Gln Met Thr Gln Thr Thr Ser Ser Leu Ser Ala Ser Leu Gly
1               5                   10                  15

Asp Arg Val Thr Ile Ser Cys
                20
```

<210> SEQ ID NO 11
<211> LENGTH: 15
<212> TYPE: PRT
<213> ORGANISM: Homo sapiens

<400> SEQUENCE: 11

```
Trp Tyr Gln Gln Lys Pro Asp Gly Thr Val Lys Leu Leu Ile Tyr
1               5                   10                  15
```

<210> SEQ ID NO 12
<211> LENGTH: 31
<212> TYPE: PRT
<213> ORGANISM: Homo sapiens

<400> SEQUENCE: 12

```
Gly Val Pro Ser Arg Phe Ser Gly Ser Gly Ser Gly Thr Asp Phe Ser
1               5                   10                  15

Leu Thr Ile Asn Asn Leu Glu Gln Glu Asp Phe Ala Thr Tyr Phe
            20                  25                  30
```

<210> SEQ ID NO 13
<211> LENGTH: 41
<212> TYPE: PRT
<213> ORGANISM: Homo sapiens

<400> SEQUENCE: 13

```
Phe Gly Gly Gly Thr Lys Leu Glu Ile Lys Arg Ala Asp Ala Ala Pro
1               5                   10                  15

Thr Val Ser Ile Phe Pro Pro Ser Glu Gln Leu Thr Ser Gly Gly
            20                  25                  30

Ala Ser Val Val Cys Phe Leu Asn Asn
        35                  40
```

```
<210> SEQ ID NO 14
<211> LENGTH: 11
<212> TYPE: PRT
<213> ORGANISM: Homo sapiens

<400> SEQUENCE: 14

Arg Ala Ser Gln Asp Ile Ser Phe Phe Leu Asn
1               5                   10

<210> SEQ ID NO 15
<211> LENGTH: 7
<212> TYPE: PRT
<213> ORGANISM: Homo sapiens

<400> SEQUENCE: 15

Tyr Thr Ser Arg Tyr His Ser
1               5

<210> SEQ ID NO 16
<211> LENGTH: 9
<212> TYPE: PRT
<213> ORGANISM: Homo sapiens

<400> SEQUENCE: 16

Gln His Gly Asn Thr Leu Pro Trp Thr
1               5

<210> SEQ ID NO 17
<211> LENGTH: 101
<212> TYPE: PRT
<213> ORGANISM: Homo sapiens

<400> SEQUENCE: 17

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Phe Phe
            20                  25                  30

Leu Asn Trp Tyr Gln Gln Lys Pro Asp Gly Thr Val Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Ser Leu Thr Ile Asn Asn Leu Glu Gln
65                  70                  75                  80

Glu Asp Phe Ala Thr Tyr Phe Cys Gln His Gly Asn Thr Leu Pro Trp
                85                  90                  95

Thr Phe Gly Gly Gly
            100

<210> SEQ ID NO 18
<211> LENGTH: 101
<212> TYPE: PRT
<213> ORGANISM: Homo sapiens

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
    50                  55                  60
```

```
Ser Gly Ser Gly Thr Glu Phe Thr Leu Thr Ile Ser Ser Leu Gln Ser
 65                  70                  75                  80

Glu Asp Phe Ala Val Tyr Tyr Cys Gln His Gly Asn Thr Leu Pro Trp
                 85                  90                  95

Thr Phe Gly Gln Gly
            100

<210> SEQ ID NO 19
<211> LENGTH: 101
<212> TYPE: PRT
<213> ORGANISM: Homo sapiens

<400> SEQUENCE: 19

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Asp Ile Ser Phe Phe
                 20                  25                  30

Leu Asn Trp Phe Gln Gln Arg Pro Gly Gln Ser Pro Arg Arg Leu Ile
             35                  40                  45

Tyr Tyr Thr Ser Arg Tyr His Ser Gly Ile Pro Pro Arg Phe Ser Gly
 50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Gln His Gly Asn Thr Leu Pro Trp
                 85                  90                  95

Thr Phe Gly Gln Gly
            100

<210> SEQ ID NO 20
<211> LENGTH: 101
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Phe Phe
                 20                  25                  30

Leu Asn Trp Tyr Gln Gln Lys Pro Gly Lys Ala Pro Lys Leu Leu Ile
             35                  40                  45

Tyr Tyr Thr Ser Arg Tyr His Ser Gly Val Pro Ser Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln His Gly Asn Thr Leu Pro Trp
                 85                  90                  95

Thr Phe Gly Gln Gly
            100

<210> SEQ ID NO 21
<211> LENGTH: 101
<212> TYPE: PRT
<213> ORGANISM: Homo sapiens

<400> SEQUENCE: 21

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Phe Phe
```

```
Leu Asn Trp Tyr Leu Gln Lys Pro Gly Gln Ser Pro Gln Leu Leu Ile
            35                  40                  45

Tyr Tyr Thr Ser Arg Tyr His Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln His Gly Asn Thr Leu Pro Trp
                 85                  90                  95

Thr Phe Gly Gln Gly
                100

<210> SEQ ID NO 22
<211> LENGTH: 101
<212> TYPE: PRT
<213> ORGANISM: Homo sapiens

<400> SEQUENCE: 22

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Asp Ile Ser Phe Phe
                20                  25                  30

Leu Asn Trp Tyr Gln Gln Lys Pro Gly Lys Ala Pro Lys Leu Leu Ile
            35                  40                  45

Tyr Tyr Thr Ser Arg Tyr His Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln His Gly Asn Thr Leu Pro Trp
                 85                  90                  95

Thr Phe Gly Gln Gly
                100

<210> SEQ ID NO 23
<211> LENGTH: 101
<212> TYPE: PRT
<213> ORGANISM: Homo sapiens

<400> SEQUENCE: 23

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Asp Ile Ser Phe Phe
                20                  25                  30

Leu Asn Trp Tyr Gln Gln Lys Pro Gly Lys Ala Pro Lys Leu Leu Ile
            35                  40                  45

Tyr Tyr Thr Ser Arg Tyr His Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln His Gly Asn Thr Leu Pro Trp
                 85                  90                  95

Thr Phe Gly Gln Gly
                100

<210> SEQ ID NO 24
<211> LENGTH: 101
<212> TYPE: PRT
<213> ORGANISM: Homo sapiens
```

<400> SEQUENCE: 24

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Gly Asn Thr Leu Pro Trp
                85                  90                  95

Thr Phe Gly Gln Gly
            100

<210> SEQ ID NO 25
<211> LENGTH: 101
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Leu Gln Lys Pro Gly Gln Ser Pro Gln Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Asn Thr Leu Pro Trp
                85                  90                  95

Thr Phe Gly Gln Gly
            100

<210> SEQ ID NO 26
<211> LENGTH: 101
<212> TYPE: PRT
<213> ORGANISM: Homo sapiens

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Gly Asn Thr Leu Pro Trp
                85                  90                  95

Thr Phe Gly Gln Gly

```
<210> SEQ ID NO 27
<211> LENGTH: 101
<212> TYPE: PRT
<213> ORGANISM: Homo sapiens

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Ile Pro Pro Arg Phe Ser Gly
    50                  55                  60

Ser Gly Tyr Gly Thr Glu Phe Thr Phe Thr Ile Ser Ser Leu Glu Ala
65                  70                  75                  80

Glu Asp Ala Ala Thr Tyr Tyr Cys Gln His Gly Asn Thr Leu Pro Trp
                85                  90                  95

Thr Phe Gly Gln Gly
            100

<210> SEQ ID NO 28
<211> LENGTH: 101
<212> TYPE: PRT
<213> ORGANISM: Homo sapiens

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Gly Asn Thr Leu Pro Trp
                85                  90                  95

Thr Phe Gly Gln Gly
            100

<210> SEQ ID NO 29
<211> LENGTH: 101
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Leu Gln Lys Pro Gly Gln Ser Pro Gln Leu Leu Ile
        35                  40                  45

Tyr Tyr Thr Ser Arg Tyr His Ser Gly Val Pro Ser Arg Phe Ser Gly
    50                  55                  60
```

```
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln His Gly Asn Thr Leu Pro Trp
                 85                  90                  95

Thr Phe Gly Gln Gly
            100

<210> SEQ ID NO 30
<211> LENGTH: 101
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Phe Phe
                 20                  25                  30

Leu Asn Trp Tyr Gln Gln Lys Pro Gly Lys Ala Pro Lys Leu Leu Ile
             35                  40                  45

Tyr Tyr Thr Ser Arg Tyr His Ser Gly Val Pro Ser Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln His Gly Asn Thr Leu Pro Trp
                 85                  90                  95

Thr Phe Gly Gln Gly
            100

<210> SEQ ID NO 31
<211> LENGTH: 101
<212> TYPE: PRT
<213> ORGANISM: Homo sapiens

<400> SEQUENCE: 31

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Phe Phe
                 20                  25                  30

Leu Asn Trp Tyr Gln Gln Lys Pro Gly Lys Ala Pro Lys Leu Leu Ile
             35                  40                  45

Tyr Tyr Thr Ser Arg Tyr His Ser Gly Ile Pro Pro Arg Phe Ser Gly
 50                  55                  60

Ser Gly Tyr Gly Thr Glu Phe Thr Phe Thr Ile Ser Ser Leu Glu Ala
 65                  70                  75                  80

Glu Asp Ala Ala Thr Tyr Tyr Cys Gln His Gly Asn Thr Leu Pro Trp
                 85                  90                  95

Thr Phe Gly Gln Gly
            100

<210> SEQ ID NO 32
<211> LENGTH: 101
<212> TYPE: PRT
<213> ORGANISM: Homo sapiens

<400> SEQUENCE: 32

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Asp Ile Ser Phe Phe
                 20                  25                  30
```

Leu Asn Trp Tyr Gln Gln Lys Pro Gly Lys Ala Pro Lys Leu Leu Ile
            35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Gly Asn Thr Leu Pro Trp
                85                  90                  95

Thr Phe Gly Gln Gly
            100

<210> SEQ ID NO 33
<211> LENGTH: 101
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
            35                  40                  45

Tyr Tyr Thr Ser Arg Tyr His Ser Gly Val Pro Ser Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Gly Asn Thr Leu Pro Trp
                85                  90                  95

Thr Phe Gly Gln Gly
            100

<210> SEQ ID NO 34
<211> LENGTH: 111
<212> TYPE: PRT
<213> ORGANISM: Homo sapiens

<400> SEQUENCE: 34

Gln Val Gln Leu Gln Gln Ser Ala Pro Glu Leu Ala Arg Pro Gly Ala
1               5                   10                  15

Ser Val Lys Met Ser Cys Thr Ala Ser Gly Tyr Ile Phe Thr Asn Tyr
            20                  25                  30

Pro Ile His Trp Val Lys Gln Arg Pro Gly Gln Gly Leu Glu Trp Ile
            35                  40                  45

Gly Phe Ile Asp Pro Gly Gly Gly Tyr Asp Glu Pro Asp Glu Arg Phe
    50                  55                  60

Arg Asp Arg Ala Thr Leu Thr Ala Asp Lys Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 35
<211> LENGTH: 111
<212> TYPE: PRT
<213> ORGANISM: Homo sapiens -continued

<400> SEQUENCE: 35

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Tyr Asp Glu Pro Asp Glu Arg Phe
    50                  55                  60

Arg Asp Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Gly Gly Tyr Tyr Leu Asp Tyr Trp Gly Gln Gly
            100                 105                 110
```

<210> SEQ ID NO 36
<211> LENGTH: 111
<212> TYPE: PRT
<213> ORGANISM: Homo sapiens

<400> SEQUENCE: 36

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Tyr Asp Glu Pro Asp Glu Arg Phe
    50                  55                  60

Arg Asp Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Gly Gly Tyr Tyr Leu Asp Tyr Trp Gly Gln Gly
            100                 105                 110
```

<210> SEQ ID NO 37
<211> LENGTH: 111
<212> TYPE: PRT
<213> ORGANISM: Homo sapiens

<400> SEQUENCE: 37

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
            20                  25                  30

Pro Ile His Trp Ile Arg Gln Ser Pro Ser Arg Gly Leu Glu Trp Leu
        35                  40                  45

Gly Phe Ile Asp Pro Gly Gly Tyr Asp Glu Pro Asp Glu Arg Phe
    50                  55                  60

Arg Asp Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly Gly Gly Tyr Tyr Leu Asp Tyr Trp Gly Gln Gly
            100                 105                 110
```

```
<210> SEQ ID NO 38
<211> LENGTH: 111
<212> TYPE: PRT
<213> ORGANISM: Homo sapiens

<400> SEQUENCE: 38

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Gly Tyr Asp Glu Pro Asp Glu Arg Phe
    50                  55                  60

Arg Asp Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 39
<211> LENGTH: 111
<212> TYPE: PRT
<213> ORGANISM: Homo sapiens

<400> SEQUENCE: 39

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Gly Tyr Asp Glu Pro Asp Glu Arg Phe
    50                  55                  60

Arg Asp Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 40
<211> LENGTH: 111
<212> TYPE: PRT
<213> ORGANISM: Homo sapiens

<400> SEQUENCE: 40

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
            20                  25                  30

Pro Ile His Trp Ile Arg Gln Pro Pro Gly Lys Gly Leu Glu Trp Ile
        35                  40                  45

Gly Phe Ile Asp Pro Gly Gly Gly Tyr Asp Glu Pro Asp Glu Arg Phe
    50                  55                  60
```

Arg Asp Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 41
<211> LENGTH: 111
<212> TYPE: PRT
<213> ORGANISM: Homo sapiens

<400> SEQUENCE: 41

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
                20                  25                  30

Pro Ile His Trp Val Arg Gln Ala Pro Gly Gln Gly Leu Glu Trp Met
            35                  40                  45

Gly Phe Ile Asp Pro Gly Gly Gly Tyr Asp Glu Pro Asp Glu Arg Phe
50                  55                  60

Arg Asp Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 42
<211> LENGTH: 111
<212> TYPE: PRT
<213> ORGANISM: Homo sapiens

<400> SEQUENCE: 42

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
                20                  25                  30

Pro Ile His Trp Ile Arg Gln Pro Pro Gly Lys Gly Leu Glu Trp Ile
            35                  40                  45

Gly Phe Ile Asp Pro Gly Gly Gly Tyr Asp Glu Pro Asp Glu Arg Phe
50                  55                  60

Arg Asp Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 43
<211> LENGTH: 111
<212> TYPE: PRT
<213> ORGANISM: Homo sapiens

<400> SEQUENCE: 43

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
            20                  25                  30

Pro Ile His Trp Ile Arg Gln Pro Pro Gly Lys Gly Leu Glu Trp Ile
        35                  40                  45

Gly Phe Ile Asp Pro Gly Gly Tyr Asp Glu Pro Asp Glu Arg Phe
    50                  55                  60

Arg Asp Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 44
<211> LENGTH: 111
<212> TYPE: PRT
<213> ORGANISM: Homo sapiens

<400> SEQUENCE: 44

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ile Phe Thr Asn Tyr
            20                  25                  30

Pro Ile His Trp Val Arg Gln Ala Thr Gly Gln Gly Leu Glu Trp Met
        35                  40                  45

Gly Phe Ile Asp Pro Gly Gly Tyr Asp Glu Pro Asp Glu Arg Phe
    50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 45
<211> LENGTH: 111
<212> TYPE: PRT
<213> ORGANISM: Homo sapiens

<400> SEQUENCE: 45

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Tyr Asp Glu Pro Asp Glu Arg Phe
    50                  55                  60

Arg Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 46
<211> LENGTH: 111

```
<212> TYPE: PRT
<213> ORGANISM: Homo sapiens

<400> SEQUENCE: 46

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Gly Tyr Asp Glu Pro Asp Glu Arg Phe
    50                  55                  60

Arg Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 47
<211> LENGTH: 111
<212> TYPE: PRT
<213> ORGANISM: Homo sapiens

<400> SEQUENCE: 47

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Gly Tyr Asp Glu Pro Asp Glu Arg Phe
    50                  55                  60

Arg Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 48
<211> LENGTH: 111
<212> TYPE: PRT
<213> ORGANISM: Homo sapiens

<400> SEQUENCE: 48

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Gly Tyr Asp Glu Pro Asp Glu Arg Phe
    50                  55                  60

Arg Asp Arg Val Thr Ile Ser Val Asp Thr Ser Lys Asn Gln Phe Ser
65                  70                  75                  80
```

Leu Lys Leu Ser Ser Val Thr Ala Ala Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 49
<211> LENGTH: 111
<212> TYPE: PRT
<213> ORGANISM: Homo sapiens

<400> SEQUENCE: 49

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Tyr Asp Glu Pro Asp Glu Arg Phe
    50                  55                  60

Arg Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 50
<211> LENGTH: 111
<212> TYPE: PRT
<213> ORGANISM: Homo sapiens

<400> SEQUENCE: 50

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
            20                  25                  30

Pro Ile His Trp Val Arg Gln Ala Thr Gly Gln Gly Leu Glu Trp Met
        35                  40                  45

Gly Phe Ile Asp Pro Gly Gly Tyr Asp Glu Pro Asp Glu Arg Phe
    50                  55                  60

Arg Asp Arg Phe Thr Ile Ser Arg Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Thr Arg Arg Gly Gly Gly Tyr Tyr Leu Asp Tyr Trp Gly Gln Gly
            100                 105                 110

<210> SEQ ID NO 51
<211> LENGTH: 33
<212> TYPE: PRT
<213> ORGANISM: Homo sapiens

<400> SEQUENCE: 51

Ser Pro Arg Trp Ser Leu Trp Ser Thr Trp Ala Pro Cys Ser Val Thr
1               5                   10                  15

Cys Ser Glu Gly Ser Gln Leu Arg Tyr Arg Arg Cys Val Gly Trp Asn
            20                  25                  30

Gly

US 8,664,362 B2

HUMANIZED AND CHIMERIC ANTI-PROPERDIN ANTIBODIES

RELATED APPLICATION

This application is a National Phase filing of PCT/US2011/027964, filed Mar. 10, 2011, which claims priority to U.S. Provisional Application Ser. No. 61/312,469, filed Mar. 10, 2010, and U.S. patent application Ser. No. 13/582,546, filed Sep. 4, 2012, which is a National Phase Filing of PCT/US2011/026841, filed Mar. 2, 2011 and claims priority to U.S. Provisional Application Ser. No. 61/309,705, filed Mar. 2, 2010. The subject matter of which are incorporated herein by reference in their entirety.

FIELD OF THE INVENTION

The present invention relates to humanized and chimeric antibodies and antigen-binding fragments thereof that can bind to properdin and selectively inhibit the alternative complement pathway in disease conditions where the alternative pathway contributes to disease pathology. These antibodies can be used to treat inflammatory diseases and disorders in humans.

BACKGROUND OF THE INVENTION

The complement system is important for clearance of pathogens and host defense against pathogens. The alternative complement pathway (AP) is activated in several pathological inflammatory conditions and autoimmune diseases. It is, therefore, clinically beneficial to inhibit disease-induced AP activation.

The complement system is activated via three distinct complement pathways; the classical, the lectin and the alternative pathways. The classical pathway is activated via antigen-antibody complexes. The lectin pathway is a variation of the classical pathway. The alternative pathway is activated by foreign material, artificial surfaces, dead tissues, bacteria, and dead yeast cells. In disease conditions, AP activation generates C3a, C5a, and C5b-9 (also known as the MAC complex). Elevated levels of C3a, C5a, and C5b-9 have been found to be associated with multiple acute and chronic disease conditions. These inflammatory molecules activate neutrophils, monocytes and platelets. Therefore, inhibition of disease-induced AP activation is important for clinical benefit in the diseases where complement activation plays a role in disease pathology.

These inflammatory molecules mediate inflammation by activating leukocytes, activation of macrophages, neutrophils, platelets, mast cells and endothelial cells, vascular permeability, cytolysis, and tissue injury. Activated cells release inflammatory mediators such as TNF-α, IL-1β, IL-6, IL-8, VEGF, neutrophil elastase, and peroxides.

The initiation of the alternative complement pathway requires the binding of properdin to C3b, which occurs with high affinity. Properdin-bound C3b (PC3b) associates with factor B to form the PC3bB complex, which is then cleaved by factor D into PC3bBb and Ba, in which Ba is released. Properdin-depleted serum completely lacks AP activation activity, showing that properdin is essential for this initiation process to occur. Properdin concentration in blood is nearly 5 ug/ml, and consequently, it is the only non-protease molecule present at much lower concentration than other non-protease molecules.

Inhibiting AP activation would be an important therapeutic strategy to mitigate symptoms and slow or prevent disease progression. Depleting, neutralizing, or inactivating properdin can block AP activation without inhibiting the classical complement pathway and, thus, is a viable and promising therapeutic strategy. The benefit of leaving the classical pathway intact is increased protection against infection.

SUMMARY OF THE INVENTION

The present invention relates to an isolated chimeric and humanized monoclonal antibody that specifically binds properdin and selectively blocks the alternative complement pathway. Chimeric, humanized, and fully human antibodies made by any methods to generate Fab, Fab', Fab2', and IgGs can neutralize properdin functional activity and prevent AP induced production of C3a, C5a, and C5b-9. As a result, cellular activation, inflammation, and release of inflammatory mediators can also be prevented. Since AP activation is linked to various acute and chronic human diseases, the blockade created with chimeric, humanized, and fully human antibodies can also block the inflammation process, providing clinical benefits to human beings treated with the anti-properdin monoclonal antibodies of the present invention.

An aspect of the invention therefore relates to an isolated anti-properdin antibody or antigen binding portion thereof that comprises a heavy chain variable domain including the 3CDRs in SEQ ID NO: 1 and light chain variable domain including the 3CDRS in SEQ ID NO: 9.

In some aspects, the anti-properdin antibody or antigen binding portion thereof comprises a heavy chain selected from the group consisting of SEQ ID NO: 1, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, and SEQ ID NO: 50.

In other aspects, the anti-properdin antibody or antigen-binding portion thereof comprises a light chain selected from the group consisting of SEQ ID NO: 9, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33.

Another aspect of the application relates to an isolated anti-properdin antibody or antigen-binding portion thereof that includes at least one CDR selected from the group consisting of: a CDR-H1 comprising the amino acid sequence of SEQ ID NO: 6; a CDR-H2 comprising the amino acid sequence of SEQ ID NO: 7; a CDR-H3 comprising the amino acid sequence of SEQ ID NO: 8; a CDR-L1 comprising the amino acid sequence of SEQ ID NO: 14; a CDR-L2 comprising the amino acid sequence of SEQ ID NO: 15; and a CDR-L3 comprising the amino acid sequence of SEQ ID NO: 16.

In some aspects, the isolated anti-properdin antibody or antigen binding portion thereof includes a CDR-L1 region polypeptide of SEQ ID NO: 14 and a CDR-H1 region polypeptide of SEQ ID NO: 6.

In other aspects, the anti-properdin antibody or antigen-binding portions thereof includes a CDR-L2 region polypeptide of SEQ ID NO: 15 and a CDR-H2-region polypeptide of SEQ ID NO: 7.

In other aspects, the anti-properdin antibody or antigen-binding portion thereof includes a CDR-L3 region polypeptide of SEQ ID NO: 16 and a CDR-H3-region polypeptide of SEQ ID NO: 8.

In still other aspects, the light chain CDR-L1 includes SEQ ID NO: 14, the light chain CDR-L2 includes SEQ ID NO: 15; and the light chain CDR-L3 includes SEQ ID NO: 16.

In a further aspect, the heavy chain CDR-H1 includes SEQ ID NO: 6; the heavy chain CDR-H2 includes SEQ ID NO: 7, and the heavy chain CDR-H3 includes SEQ ID NO: 8.

In another aspect, the light chain CDR-L2 includes SEQ ID NO: 14, the light chain CDR-L2 includes SEQ ID NO: 15; the light chain CDR-L3 includes SEQ ID NO: 16; the heavy chain CDR-H1 includes SEQ ID NO: 6; the heavy chain CDR-H2 includes SEQ ID NO: 7; and the heavy chain CDR-H3 includes SEQ ID NO: 8.

In other aspects, the anti-properdin antibody or antigen-binding portion thereof includes at least two CDRs selected from the group consisting of: the CDR-H1 comprising the amino acid sequence of SEQ ID NO: 6; the CDR-H2 comprising the amino acid sequence of SEQ ID NO: 7; the CDR-H3 comprising the amino acid sequence of SEQ ID NO: 8; the CDR-L1 comprising the amino acid sequence of SEQ ID NO: 14; the CDR-L2 comprising the amino acid sequence of SEQ ID NO: 15; and the CDR-L3 comprising the amino acid sequence of SEQ ID NO: 16.

In other aspects, the anti-properdin antibody or antigen-binding portion thereof includes at least three CDRs selected from the group consisting of: the CDR-H1 comprising the amino acid sequence of SEQ ID NO: 6; the CDR-H2 comprising the amino acid sequence of SEQ ID NO: 7; the CDR-H3 comprising the amino acid sequence of SEQ ID NO: 8; the CDR-L1 comprising the amino acid sequence of SEQ ID NO: 14; the CDR-L2 comprising the amino acid sequence of SEQ ID NO: 15; and the CDR-L3 comprising the amino acid sequence of SEQ ID NO: 16.

In other aspects, the anti-properdin antibody or antigen-binding portion thereof includes at least four CDRs selected from the group consisting of: the CDR-H1 comprising the amino acid sequence of SEQ ID NO: 6; the CDR-H2 comprising the amino acid sequence of SEQ ID NO: 7; the CDR-H3 comprising the amino acid sequence of SEQ ID NO: 8; the CDR-L1 comprising the amino acid sequence of SEQ ID NO: 14; the CDR-L2 comprising the amino acid sequence of SEQ ID NO: 15; and the CDR-L3 comprising the amino acid sequence of SEQ ID NO: 16.

In other aspects, the anti-properdin antibody or antigen-binding portion thereof includes at least five CDRs selected from the group consisting of: the CDR-H1 comprising the amino acid sequence of SEQ ID NO: 6; the CDR-H2 comprising the amino acid sequence of SEQ ID NO: 7; the CDR-H3 comprising the amino acid sequence of SEQ ID NO: 8; the CDR-L1 comprising the amino acid sequence of SEQ ID NO: 14; the CDR-L2 comprising the amino acid sequence of SEQ ID NO: 15; and the CDR-L3 comprising the amino acid sequence of SEQ ID NO: 16.

In yet other aspects, the anti-properdin antibody or antigen binding portion thereof includes a heavy chain variable domain having at least 90% sequence identity to an amino acid sequence of SEQ ID NO: 1.

In still other aspects, the anti-properdin antibody or antigen binding portion thereof includes a light chain variable domain having at least 90% sequence identity to an amino acid sequence of SEQ ID NO: 9.

In a further aspect, the anti-properdin antibody comprises a heavy chain variable domain having at least 90% sequence identity to an amino acid sequence selected from SEQ ID NO: 1 and a light chain variable domain having at least 90% sequence identity to an amino acid sequence selected from SEQ ID NO: 9.

In another aspect, the anti-properdin antibody or antigen binding portion thereof includes a heavy chain variable domain selected from the group consisting of: SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 SEQ ID NO: 47 SEQ ID NO: 48 SEQ ID NO: 49, and SEQ ID NO: 50.

In a further aspect the anti-properdin antibody or antigen binding portion includes a light chain variable domain selected from the group consisting of: SEQ ID NO: 18, SEQ ID NO: 19, SEQ ID NO:20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33.

Another aspect of the invention relates to a method of inhibiting alternative complement pathway activation in a mammal. The method includes the step of administering of an isolated anti-properdin antibody or antigen binding portion thereof to a human or other mammal that specifically binds to properdin and inhibits alternative complement pathway activation. The isolated anti-properdin antibody or antigen binding portion thereof includes a heavy chain variable domain including the 3CDRs in SEQ ID NO: 1 and light chain variable domain including the 3CDRS in SEQ ID NO: 9.

In another aspect, the method includes the step of treating a disease or disorder in which activation of the alternative complement pathway plays a role, comprising administering a chimeric or humanized anti-properdin antibody or antigen-binding fragment thereof to an individual that has, or is at risk of developing, said disease or disorder.

In a further aspect, the method includes the step of treating a disease or disorder selected from the group consisting of inflammatory diseases and inflammatory disorders.

In another aspect, the method includes the step of treating a disease or disorder selected from the group consisting of autoimmune diseases and autoimmune disorders.

In a further aspect, the method includes the step of treating an autoimmune disease or autoimmune disorder selected from the group consisting of systemic lupus erythematosus, myasthenia gravis, arthritis condition, Alzheimer's disease and multiple sclerosis.

In another aspect, the method includes the step of treating an arthritis condition. The arthritis condition can be selected from the group consisting of rheumatoid arthritis, osteo-arthritis, and juvenile arthritis.

In a further aspect, the method includes the step of treating a complement-associated disease or disorder selected from a group consisting of ocular diseases and ocular disorders. The ocular disease or ocular disorder can be selected from the group consisting of diabetic retinopathy, histoplasmosis of the eye, age-related macular degeneration, diabetic retinopathy, choroidal neo-vascularization (CNV), uveitis, diabetic macular edema, pathological myopia, von Hippel-Lindau disease, histoplasmosis of the eye, Central Retinal Vein Occlusion (CRVO), corneal neo-vascularization, and retinal neovascularization. The age-related macular degeneration can be selected from the group consisting of intermediate dry AMD and geographic atrophy.

In another aspect, the step of treating a complement-associated disorder is selected from the group consisting of asthmatic disorders and airway inflammation disorders. The airway inflammation disorder can be selected from the group consisting of: asthma, chronic obstructive pulmonary disease ("COPD"), allergic broncho-pulmonary aspergillosis, hypersensitivity pneumonia, eosinophilic pneumonia, emphysema, bronchitis, allergic bronchitis bronchiecstasis, cyctic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus ("RSV") infection, parainfluenza virus ("PIV") infection, rhinovirus ("RV") infection, and adenovirus infection.

BRIEF DESCRIPTION OF THE DRAWINGS

FIG. 13 shows that an anti-properdin antibody inhibits ischemia reperfusion injury in rabbits.

FIG. 16 shows the heavy chain amino acid sequences SEQ ID NO: 1 through SEQ. ID NO: 8.

FIG. 17 shows the light chain amino acid sequences SEQ ID NO: 9 through SEQ ID NO: 16.

FIG. 21 shows the light chain amino acid sequences SEQ ID NO: 17 through SEQ ID NO: 21.

FIG. 22 shows the light chain amino acid sequence SEQ ID NO: 22 through SEQ ID NO: 27.

FIG. 23 shows the light chain amino acid sequences SEQ ID NO: 28 through SEQ ID NO: 33.

FIG. 24 shows the heavy chain amino acid sequences SEQ ID NO: 34 through SEQ ID NO: 39.

FIG. 25 shows the heavy chain amino acid sequences SEQ ID NO: 40 through SEQ ID NO: 45.

FIG. 26 shows the heavy chain amino acid sequences SEQ ID NO: 46 through SEQ ID NO: 50.

FIG. 29 shows the properdin sequence as an epitope for this antibody.

DETAILED DESCRIPTION OF THE INVENTION

Figure 1:
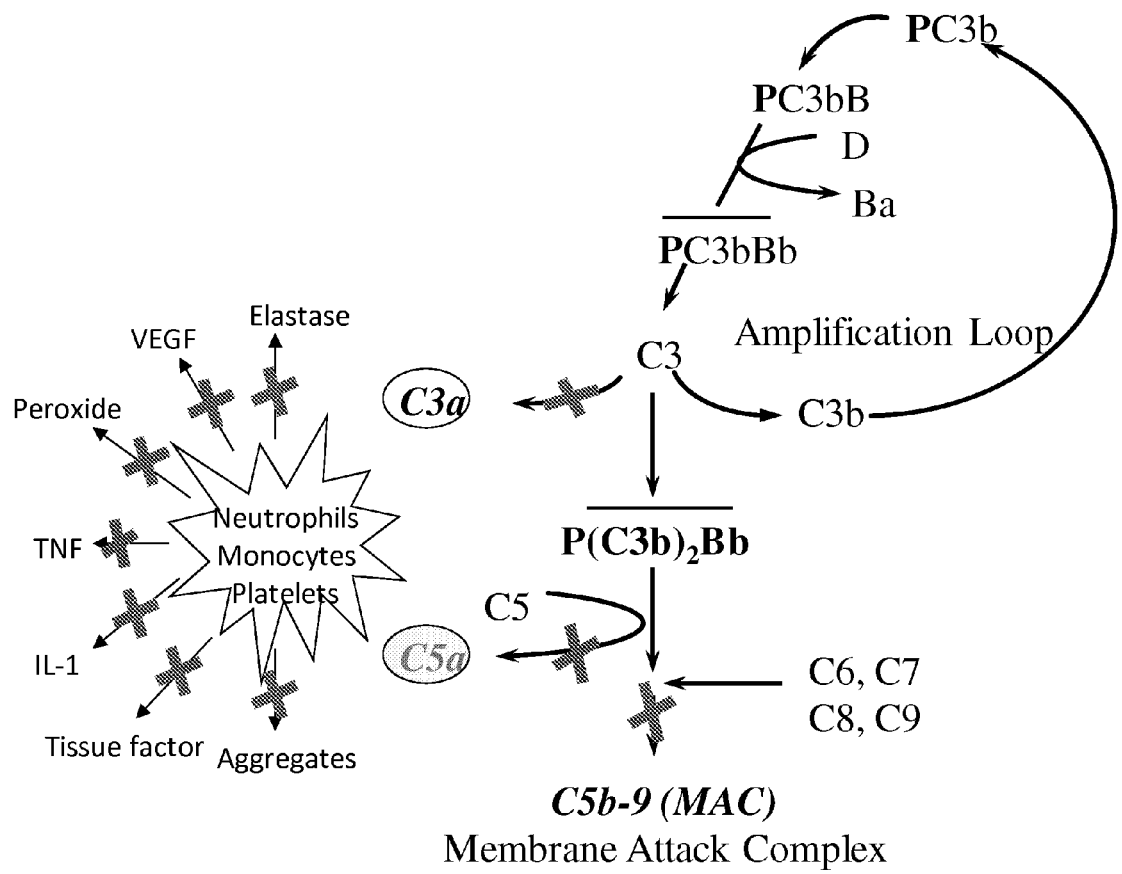
FIG. 1 shows the schematics of alternative complement pathway, including the target protein properdin.

As used herein, the term "acceptor human framework" refers to a framework comprising the amino acid sequence of a VL or VH framework derived from a human immunoglobulin framework, or from a human consensus framework.

As used herein, the term "antibody" covers full length monoclonal antibodies, polyclonal antibodies, nanobodies and multi-specific antibodies. Biological antibodies are usually hetero-tetrameric glycoproteins of about 150,000 Daltons, composed of two identical light (L) chains and two identical heavy (H) chains. The two heavy chains are linked together by disulfide bonds, and each heavy chain is linked to a light chain by a disulfide bond. Each full-length IgG molecule contains at least two binding sites for a specific target or antigen. Light chains are either kappa or the lambda. Both light chains contain a domain of variable amino acid sequences, called the variable region (variously referred to as a "$V_L$," "$V_{kappa}$," or "$V_{lambda}$-region") and a domain of relatively conserved amino acid sequences, called the constant region ("CL-region"). Similarly, each heavy chain contains a variable region ("$V_H$-region") and three constant domains ("$C_{H1}$-," "$C_{H2}$-," and "$C_{H3}$-regions") and a hinge region.

As used herein, the term "antibody fragment" refers to a segment of a full-length antibody, generally called as the target binding or variable region. Examples include Fab, Fab', F(ab')2 and Fv fragments. An "Fv" fragment is the minimum antibody fragment which contains a complete target recognition and binding site.

As used herein, the term "antigen binding fragment" refers to a fragment or fragments of an antibody molecule that contain the antibody variable regions responsible for antigen binding. Fab, Fab', and F(ab)$_2$ lack the F$_C$ regions. Antigen-binding fragments can be prepared from full-length antibody by protease digestion. Antigen-binding fragments may be produced using standard recombinant DNA methodology by those skilled in the art.

As used herein, complementarity-determining region ("CDR") refers to a specific region within variable regions of the heavy and the light chain. Generally, the variable region consists of four framework regions (FR1, FR2, FR3, FR4) and three CDRs arranged in the following manner: NH$_2$—FR1-CDR1-FR2-CDR2-FR3-CDR3-FR4-COOH. The term "framework regions" refers to those variable domain residues other than the CDR residues herein defined.

As used herein, the term "epitope" refers to a site on properdin to which antibody and fragments thereof bind and perform the functional activity. The term epitope is the same as "antigenic site", and "antibody binding site,". Both murine monoclonal mAb$^{71-110}$ and the chimeric and humanized antibodies and the binding fragments thereof of the present invention share the same binding site. The murine mAb has been described in PCT Application No. PCT/US2008/068530. One skilled in the art can align the sequence of properdin of a human with the sequence of properdin from another animal species and determine the positions of the epitope.

As used herein, "Fab fragment" refers to the constant domain of the light chain and the first constant domain of the heavy chain. Fab' fragments differ from Fab fragments by the few extra residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product.

As used herein, the term "functional fragment" of an antibody refers to an antibody fragment having qualitative biological activity in common with a full-length antibody. For example, a functional antibody fragment is one which can bind to properdin in such a manner so as to prevent or substantially reduce the alternative complement activation.

As used herein, the term "human consensus framework" refers to a framework which represents the most commonly occurring amino acid residue in a selection of human immunoglobulin VL or VH framework sequences. Generally, the selection of human immunoglobulin VL or VH sequences is from a subgroup of variable domain sequences.

As used herein, a "humanized antibody" refers to an antibody consisting of mostly human sequences, except for CDR1, CDR2, and CDR3. All framework regions are also humanized. A chimeric antibody comprises murine CDRs, murine framework regions, and human constant regions. Collectively, chimeric antibodies contain murine both variable regions and human constant regions.

As used herein, the term "identical" or "substantially identical" with respect to an antibody chain polypeptide sequence may be construed as an antibody chain exhibiting at least 65%, 70%, 80%, 90% or 95% sequence identity to the reference polypeptide sequence present in the variable region of the antigen binding fragment. The term with respect to a nucleic acid sequence may be construed as a sequence of nucleotides exhibiting at least about 65%, 75%, 85%, 90%, 95% or 97% sequence identity to the reference nucleic acid sequence.

As used herein, the term "individual" refers to a vertebrate, preferably a mammal and more preferably a human. Individuals amenable to treatment include those who are presently asymptomatic, but who are at risk of developing a symptomatic disorder in which the alternative complement pathway plays a role, or in which activation of the alternative complement pathway plays a role.

As used herein, the term "mammal" refers to any animal classified as a mammal includes humans, higher primates, domestic and farm animals, horses, pigs, cattle, dogs, cats and ferrets, etc. In one embodiment of the invention, the mammal is a human.

As used herein, "monoclonal antibody" refers to a homogeneous population of antibodies. Such antibodies are highly specific and are directed against a single target antigen. These monoclonal antibodies are homogeneously produced by the hybridoma culture, uncontaminated by other immunoglobulins. Monoclonal antibodies can also be produced by other procedures such as phase display by well known methods.

As used herein, the term "native sequence properdin" refers to naturally-occurring precursor forms of properdin, naturally-occurring variant forms, and naturally-occurring allelic variants of properdin, as well as structural conformational variants of properdin molecules having the same amino acid sequence as a properdin polypeptide derived from nature. Properdin polypeptides of non-human animals, including higher primates and non-human mammals, are included within this definition.

As used herein, the term "properdin" refers to native sequence and variant properdin polypeptides.

As used herein, the term "SDR" refers to all or a portion of the amino acid sequence of the third complementarity determining region ("CDR3") and the fourth framework region ("FR4") of an IgG or fragments thereof.

As used herein, the term "selectively inhibit the alternative complement pathway" refers to preferentially and exclusively inhibits the alternative complement pathway, but does not inhibit other pathways for complement activation, including the classical complement pathway. For example, the humanized and chimerized antibodies and their antigen-binding fragments selectively inhibits the alternative complement pathway. This definition applies to other methods described herein wherein the alternative complement pathway is selectively inhibited.

As used herein, the term "therapeutically effective amount" refers to the amount of an "properdin antagonist" which is required to achieve a measurable improvement in the state, for example, pathology, of the target disease or condition, such as, for example, a complement-associated eye condition.

As used herein, the term "treatment" refers to both therapeutic treatment and prophylactic or preventative measures.

The present invention can provide anti-properdin agents that are useful for the prevention and treatment of complement-associated conditions. These anti-properdin agents can include, but are not limited to, anti-properdin antibodies and antibody variants thereof, antigen-binding fragments thereof, other binding polypeptides, peptides, non-peptide small molecules, aptamers, and DNA and RNA fragments. These anti-properdin agents can bind to properdin and can be capable of neutralizing, blocking, partially or fully inhibiting, abrogating, reducing or interfering with properdin functional activities, for example the ability of properdin to participate in the pathology of any complement-associated inflammatory disease or disorder.

The anti-properdin agent of the present invention can prevent the binding of properdin to C3b to form the PC3b complex by selectively binding to properdin. As a result, the PC3b complex and the PC3bBb complex will not form. Since the PC3bBb complex cleaves C5 into C5a and C5b, the MAC complex (C5b-9) also will not form. Thus, by inhibiting the binding of properdin to C3b, the anti-properdin agent of the present invention will inhibit the formation of the MAC complex. Elevated levels of the MAC complex have been found to be associated with multiple acute and chronic disease conditions. Therefore, inhibition of the MAC complex via the anti-properdin agent of the present invention is important for clinical benefit in the diseases where complement activation plays a role in disease pathology.

The PC3b complex, the PC3bB complex, and the PC3bBb complex can all be polymerized Inhibiting the polymerization of each of these complexes, where the molar ratio of properdin to each of C3b, factor B, or factor Bb is 1:1, with an anti-properdin agent is known. The anti-properdin agent of the present invention can inhibit the polymerization of each of these complexes with an anti-properdin agent, where each of these complexes comprises at least one more mole properdin than to each of, C3b, factor B, and factor Bb in each complex respectively. In one example, for the PC3b complex, the molar ratio between properdin and C3b can be expressed as $(P)_X(C3b)_Y$, where X=Y+1. In another example, for the PC3bB complex, the molar ratio between properdin, C, C3b, and factor B can be expressed as $(P)_X(C3b)_Y(B)_Z$, where X=Y+Z. This example also can express the molar ratio of properdin to C3b and factor Bb in the PC3bBb complex.

The anti-properdin agent of the present invention can have the ability to inhibit any biological activity of properdin. Such activity can bring a measurable improvement in the state of pathology of properdin-associated disease or condition, for example, a complement-associated inflammatory disease or disorder. The activity can be evaluated in in vitro or in vivo tests, including, but not limited to, binding assays, alternative pathway hemolysis assays using a relevant animal model, or human clinical trials.

In another embodiment of the invention, the anti-properdin agent can bind to a specific epitope located on properdin to inhibit AP activation. In one example, the anti-properdin agent can bind to the N-terminal domain of properdin to inhibit the binding of properdin to C3b. The epitope mapping sequence for the anti-properdin agent of the present invention is characterized as SEQ ID NO: 51.

The anti-properdin agent of the present invention can include a humanized monoclonal anti-properdin antibody or antigen-binding fragments thereof that selectively binds to properdin and selectively inhibit activation of the alternative complement pathway can be used to treat any alternative pathway associated inflammatory diseases or disorders in humans or other mammals. A comprehensive list of diseases and disorders is included herein.

A human anti-properdin antibody can include an antibody which specifically binds to human properdin in such a manner so as to inhibit or substantially reduce complement activation in a human. The present invention can also relate to a method of reducing inflammation caused by the complement mediated inflammatory diseases or disorders to provide clinical benefits to a human.

The present invention can include a method of production and use of humanized anti-properdin antibodies, and fragments thereof. Methods for making humanized non-human antibodies are well known in the art. Humanization is essentially performed by substituting rodent CDRs or CDR sequences for the corresponding sequences of a human antibody. The choice of human variable domains, both light and heavy, to be used in making the humanized antibodies can, in some instances, be important to reduce antigenicity and/or human anti-mouse antibody (HAMA) response. The present invention can provide antibodies that are humanized such that HAMA response is reduced or eliminated. Any antibody, whether chimeric, humanized, or human, can bind properdin and inhibit AP-dependent hemolysis of rabbit erythrocytes.

Ordinarily, properdin can have a range of percentages of amino acid sequence identity, ranging from at least about 60%, to at least about 70%, to at least about 80%, to at least about 85%, to at least about least about 90%, to at least about 95%, to at least about 98%, to at least about 99% amino acid sequence identity with the mature human amino acid sequence.

The variable domain of the antibodies refers to certain portions of the variable domains that differ in sequence among antibodies. The variability in the antibodies of the present invention can be concentrated in three CDR segments, located in both the light chain and the heavy chain variable domains. The highly conserved portions of variable domains are called framework (FR) regions. In the anti-properdin antibodies of the present invention, there are four FR regions, connected by three CDRs, that can comprise a variable chain. The CDRs in each of the light and heavy chains are held together in close proximity by the FR regions and, with the CDRs from the other chain, can contribute to the formation of the target binding site of antibodies.

Antibody Humanization is a process that can generate engineered human antibodies with variable region ("V-region") sequences that are substantially similar to actual human germ-line sequences, while retaining the binding specificity and affinity of a reference antibody, for example ATCC Accession Number PTA-9019 or ATCC Accession Number PTA-10649. This process can graft, for example, the CDR1, CDR2, and CDR3 regions of the heavy and the light chain sequences into humanized human framework that is both optimized and previously identified prior to the start of the grafting process. The variable region containing humanized framework can be produced into Fab, Fab', or Fab2 single chain antigen-binding antibody fragments. The resulting engineered humanized antibody fragments can retain the binding specificity of the parent murine antibody for the antigen properdin, and can have an equivalent or higher binding affinity for a specific antigen than the parent antibody. The engineered antigen binding fragments can have heavy and light chain V-regions with a high degree of amino acid sequence identity compared to the closest human germline antibody genes. For example, additional maturational changes can be introduced in the CDR3 regions of each chain during construction in order to identify antibodies with optimal binding kinetics.

The chimeric and humanized variant of the anti-properdin monoclonal antibody or antigen-binding fragment thereof can administered to an individual in conjunction with other molecules that have physiological effects, for example, a therapeutic agent. The administration of the anti-properdin monoclonal antibody in combination with at least one therapeutic agent can occur by administering the anti-properdin monoclonal antibody and the at least one therapeutic agent either simultaneously or subsequently.

Formulations or Compositions Relating to Embodiments of the Invention

The present invention can include a formulation or composition comprising an inhibitor of the alternative complement pathway and a selective inhibitor including, but not limited to, a murine, chimeric, or human antibody that prevents alternative pathway activation in a mammal. The formulation comprises: (a) an inhibitor of the alternative complement pathway as described herein; and (b) a pharmaceutically acceptable carrier. In one embodiment of the present invention, the formulation or composition can include one or more additional agents, such as an anti-inflammatory agent suitable for reducing inflammation in a mammal that has, or is at risk of developing, an inflammatory disorder. In another embodiment of the present invention, the formulation or composition can include one or more additional agents, such as an additional agent suitable for preventing or reducing ischemia-reperfusion injury in a mammal. In yet another embodiment of the present invention, the formulation or composition can include one or more additional agents, such as an additional agent suitable for treatment of another disease or condition associated with activation of the alternative complement pathway.

In another embodiment, the antibody can be a diabody, where both Fabs in the molecule are derived from two different antigens, including one from anti-properdin and the other from any other antigen.

Anti-properdin agents can be included with a pharmaceutically acceptable carrier, including, but not limited to, pharmaceutically acceptable excipients and/or pharmaceutically acceptable delivery vehicles, which are suitable for use in the administration of a formulation or composition to a suitable in vivo site.

One type of pharmaceutically acceptable carrier can include a controlled-release formulation that is capable of slowly releasing a composition of the present invention into a mammal. As used herein, a controlled-release formulation comprises an agent of the present invention in a controlled-release vehicle. Suitable controlled-release vehicles can include, but are not limited to, biocompatible polymers, other polymeric matrices, capsules, microcapsules, microparticles, bolus preparations, osmotic pumps, diffusion devices, liposomes, lipospheres, and transdermal delivery systems. Other suitable carriers can include any carrier that can be bound to or incorporated with the anti-properdin agent that extends that half-life of the anti-properdin agent to be delivered. Such a carrier can include any suitable protein carrier or a fusion segment that extends the half-life of a protein when delivered in vivo. Suitable delivery vehicles can include, but are not limited to liposomes, viral vectors or other delivery vehicles, including ribozymes, and natural lipid-containing delivery vehicles such as cells and cellular membranes.

Intravenous, intraperitoneal, intramuscular and intramuscular administrations can be performed using methods standard in the art. Aerosol delivery can be performed using methods standard in the art. Devices for delivery of aerosolized formulations can include, but are not limited to, pressurized metered dose inhalers ("MDI"), dry powder inhalers ("DPI"), and metered solution devices ("MSI"), and include devices that are nebulizers and inhalers.

Another type of dose of an antibody of the present invention, particularly when the antibody formulation is delivered by nebulization, comprises a collection of ranges between about 200 ng/kg and about 600 µg/kg body weight of the mammal, between about 200 ng/kg and about 500 µg/kg, between about 200 ng/kg and about 400 µg/kg, between about 200 ng/kg and about 300 µg/kg, between about 200 ng/kg and about 200 µg/kg, between about 200 ng/kg and about 100 µg/kg, and preferably, between about 200 ng/kg and about 50 µg/kg body weight of the mammal.

The antibodies of the present invention can be conjugated with a synthetic or biological entity at the —SH group, or any other position which does not interfere with the binding. Such conjugates can also be covered in the present invention.

Disease Conditions

In another aspect of the invention, the antibodies of the present invention can be used to inhibit complement activation via the alternative pathway in vivo in subjects, including humans, suffering from an acute or chronic pathological injury. The present invention can be used in conjunction with the following diseases, disorders, injuries, and treatments, including but not limited to:

Extracorporeal circulation diseases and disorders: Post-cardiopulmonary bypass inflammation, post-operative pulmonary dysfunction, cardiopulmonary bypass, hemodialysis, leukopheresis, plasmapheresis, plateletpheresis, heparin-induced extracorporeal LDL precipitation (HELP), postperfusion syndrome, extracorporeal membrane oxygenation (ECMO), cardiopulmonary bypass (CPB), post-perfusion syndrome, systemic inflammatory response, and multiple organ failure.

Cardiovascular diseases and disorders: acute coronary syndromes, Kawaski disease (arteritis), Takayasu's arteritis, Henoch-Schonlein purpura nephritis, vascular leakage syndrome, percutaneous coronary intervention (PCI), myocardial infarction, ischemia-reperfusion injury following acute myocardial infarction, atherosclerosis, vasculitis, immune complex vasculitis, vasculitis associated with rheumatoid arthritis (also called malignant rheumatoid arthritis), systemic lupus erythematosus-associated vasculitis, sepsis, arteritis, aneurysm, cardiomyopathy, dilated cardiomyopathy, cardiac surgery, peripheral vascular conditions, renovascular conditions, cardiovascular conditions, cerebrovascular conditions, mesenteric/enteric vascular conditions, diabetic angiopathy, venous gas embolus (VGE), Wegener's granulomatosis, heparin-induced extracorporeal membrane oxygenation, and Behcet's syndrome.

Bone/Musculoskeletal diseases and disorders: arthritis, inflammatory arthritis, non-inflammatory arthritis, rheumatoid arthritis, juvenile rheumatoid arthritis, systemic juvenile rheumatoid arthritis, osteoarthritis, osteoporosis, systemic lupus erythematosus (SLE), Behcet's syndrome, and Sjogren's syndrome.

Transplantation diseases and disorders: transplant rejection, xenograft rejection, graft versus host disease, xenotransplantation of organs or grafts, allotransplantation of organs or grafts, and hyperacute rejection.

Eye/Ocular diseases and disorders: wet and dry age-related macular degeneration (AMD), choroidal neurovascularization (CNV), retinal damage, diabetic retinopathy, diabetic retinal microangiopathy, histoplasmosis of the eye, uveitis, diabetic macular edema, diabetic retinopathy, diabetic retinal microangiopathy, pathological myopia, central retinal vein occlusion (CRVO), corneal neovascularization, retinal neovascularization, retinal pigment epithelium (RPE), histoplasmosis of the eye, and Purtscher's retinopathy.

Hemolytic/Blood diseases and disorders: sepsis, systemic inflammatory response syndrome" (SIRS), hemorrhagic shock, acute respiratory distress syndrome (ARDS), catastrophic anti-phospholipid syndrome (CAPS), cold agglutinin disease (CAD), autoimmune thrombotic thrombocytopenic purpura (TTP), endotoxemia, hemolytic uremic syndrome (HUS), atypical hemolytic uremic syndrome (aHUS), paroxysmal nocturnal hemoglobinuria (PNH), sepsis, septic shock, sickle cell anemia, hemolytic anemia, hypereosinophilic syndrome, and anti-phospholipid syndrome (APLS).

Respiratory/Pulmonary diseases and disorders: asthma, Wegener's granulomatosis, transfusion-related acute lung injury (TRALI), antiglomerular basement membrane disease (Goodpasture's disease), eosinophilic pneumonia, hypersensitivity pneumonia, allergic bronchitis bronchiecstasis, reactive airway disease syndrome, respiratory syncytial virus (RSV) infection, parainfluenza virus infection, rhinovirus infection, adenovirus infection, allergic bronchopulmonary aspergillosis (ABPA), tuberculosis, parasitic lung disease, adult respiratory distress syndrome, chronic obstructive pulmonary disease (COPD), sarcoidosis, emphysema, bronchitis, cystic fibrosis, interstitial lung disease, acute respiratory distress syndrome (ARDS), transfusion-related acute lung injury, ischemia/reperfusion acute lung injury, byssinosis, heparin-induced extracorporeal membrane oxygenation, anaphylactic shock, and asbestos-induced inflammation.

Central and Peripheral Nervous System/Neurological diseases and disorders: multiple sclerosis (MS), myasthenia gravis (MG), myasthenia gravis, multiple sclerosis, Guillain Bane syndrome, Miller-Fisher syndrome, stroke, reperfusion following stroke, Alzheimer's disease, multifocal motor neuropathy (MMN), demyelination, Huntington's disease, amyotrophic lateral sclerosis (ALS), Parkinson's disease, degenerative disc disease (DDD), meningitis, cranial nerve damage from meningitis, variant Creutzfeldt-Jakob Disease (vCJD), idiopathic polyneuropathy, brain/cerebral trauma (including, but not limited to, hemorrhage, inflammation, and edema), and neuropathic pain.

Trauma-induced injuries and disorders: hemorrhagic shock, hypovolemic shock, spinal cord injury, neuronal injury, cerebral trauma, cerebral ischemia reperfusion, crush injury, wound healing, severe burns, and frostbite.

Renal diseases and disorders: renal reperfusion injury, poststreptococcal glomerulonephritis (PSGN), Goodpasture's disease, membranous nephritis, Berger's Disease/IgA nephropathy, mesangioproliferative glomerulonephritis, membranous glomerulonephritis, membranoproliferative glomerulonephritis (mesangiocapillary glomerulonephritis), acute postinfectious glomerulonephritis, cryoglobulinemic glomerulonephritis, lupus nephritis, Henoch-Schonlein purpura nephritis, and renal cortical necrosis (RCN).

Reperfusion injuries and disorders of organs: including but not limited to heart, brain, kidney, and liver.

Reproduction and urogenital diseases and disorders: painful bladder diseases and disorders, sensory bladder diseases and disorders, spontaneous abortion, male and female diseases from infertility, diseases from pregnancy, fetomaternal tolerance, pre-eclampsia, urogenital inflammatory diseases, diseases and disorders from placental dysfunction, diseases and disorders from miscarriage, chronic abacterial cystitis, and interstitial cystitis.

Skin/Dermatologic diseases and disorders: burn injuries, psoriasis, atopic dermatitis (AD), eosinophilic spongiosis, urticaria, thermal injuries, pemphigoid, epidermolysis bullosa acquisita, autoimmune bullous dermatoses, bullous pemphigoid, scleroderma, angioedema, hereditary angioneurotic edema (HAE), erythema multiforme, herpes gestationis, Sjogren's syndrome, dermatomyositis, and dermatitis herpetiformis.

Gastrointestinal diseases and disorders: Crohn's disease, Celiac Disease/gluten-sensitive enteropathy, Whipple's disease, intestinal ischemia, inflammatory bowel disease, and ulcerative colitis.

Endocrine diseases and disorders: Hashimoto's thyroiditis, juvenile lymphocytic thyroiditis, stress anxiety, and other diseases affecting prolactin, growth or insulin-like growth factor, adrenocorticotropin release, pancreatitis, Addison's disease, diabetic conditions including, but not limited to, type 1 and type 2 diabetes, type I diabetes mellitus, sarcoidosis, diabetic retinal microangiopathy, non-obese diabetes (IDDM), angiopathy, neuropathy or retinopathy complications of IDDM or Type-2 diabetes, and insulin resistance.

Treatment of Malignancies: diseases and disorders arising from chemotherapeutics and radiation therapy.

EXAMPLES

Mouse hybridoma cells were cultured according to established procedures. The cells were collected and messenger RNA ("mRNA") was extracted from the cell pellet by standard procedures known to one skilled in the art. First strand complementary DNA ("cDNA") was generated from the purified mRNA by primer extension with oligoDT primers according to standard methods known to one skilled in the art. The cDNA was used as template for amplification of the antibody V-region sequences using degenerate primers according to standard procedures. Kappa light chain variable domains were amplified from cDNA using BioAtla's proprietary set of mouse specific kappa primers. The forward primers are designed to amplify the mouse light chain variable domains in combination with a kappa specific reverse primer. Seven different primer combinations (mK2, mK3, mK7, mK8, mK9, mk10, mK11) resulted in a PCR product of the expected size. PCR products were gel purified, TOPO-TA cloned and sequenced. Sequence analysis revealed that primer combinations mK2, mK3, mK7, mK8, mK9, and mK11 amplified the same light chain sequence (with only minor variations based on primer ambiguities. These clones have a stop codon in the CDR3/Framework 4 region yielding a non productive V-J rearrangement. This sequence is commonly found in hybridomas made with fusion partners derived from the original MOPC-21 tumor The amount of this transcript can exceed the amount of the productive light chain mRNA. Sequence analysis of the clones derived with primer combination mk10 showed that a single light chain was amplified. In order to verify the N-terminus of the obtained sequence, an additional PCR reaction was performed with a forward primer annealing to the secretion signal and a reverse primer specific for the CDR3 in clone mK10. The exact same DNA sequence was obtained with the second primer set. Heavy chain variable domains were amplified from cDNA using BioAtla's proprietary set of mouse specific heavy chain primers. The forward primers are designed to amplify the mouse heavy chain variable domains in combination with an IgG1/2 specific reverse primer. Five different primer combinations (mH1, mH2, mH4, mH5, and mH6 resulted in a PCR product of the expected size. PCR products were gel purified, TOPO-TA cloned and sequenced Sequence analysis revealed that primer mH2 amplified only non-antibody specific mouse transcripts.

Primer combinations mH4 and mH5 amplified the same transcript. It is a non-productive rearranged heavy chain, which has been described in the literature, for example, Genbank entry FJ147352. Primer combinations mH1 and mH6 resulted in 3 clones with slight amino acid variations. Three amino acid differences in framework 1 (aa positions 7 to 9) are due to primer sequences. The amino acid change at position 64 is probably caused by a PCR error. A BLAST search against the mouse genome was performed in order to identify the corresponding germline V region gene. Mouse germline gene IgH1-4 was identified as closest match (89% identity). An additional PCR reaction was performed with a forward primer specific for the N-terminus of germline gene IgH1-4 and a reverse primer specific for CDR H3 identified in the previous steps. The resulting PCR product was TOPO-TA cloned and 10 clones were sequenced. All clones had the exact same sequence.

Cloning of heavy and light chain variable domains into mammalian expression system. The previously identified variable domains (light chain clone mK10, heavy chain clone mH6-3 g) were cloned into BioAtla's proprietary mammalian expression system. The light chain variable domain is fused in frame to a human kappa constant region; the heavy chain variable domain is fused in frame to a human IgG1 constant region. Both genes are preceded by a leader peptide for secretion of full length IgG1 antibodies into the medium. Five clones were sequenced to confirm the integrity and sequences of LC and HC reading frames transfer into the expression vector. All clones contain the correct sequence (data not shown). One clone was selected for the expression tests: clone BAP010_1. Glycerol stock of clone BAP010_1 was prepared and endotoxin-free plasmid DNA was prepped for expression tests in CHO cells. Expression and functional characterization of recombinant BAP010_1.

Clone BAP010_1 was transfected into CHO-S cells and cell culture supernatant was collected at 48 hours, 72 hours, 96 hours and 120 hours post transfection. In parallel vector only was transfected into CHO-S cells. The negative controls were treated the same way as clone BAP010_1 and supernatant was collected at the same time points.

Quantitation ELISA: The amount of IgG in cell culture supernatant was determined using ELISA assay described under methods. Humanization of BAP010_001 was initiated upon confirmation of functional activity in the chimeric antibody. Double stranded DNA fragments coding for the light chain and heavy chain CDR sequences from clone BAP010_1 were combined with BioAtla's proprietary pools of human frameworks. Full length variable domains were then cloned into BioAtla's mammalian expression vector. Forty-eight light chain and 48 heavy chain sequences were analyzed to verify correct assembly of CDR and framework fragments and the diversity of the library (data not shown).

Clones were pooled and frozen as glycerol stock for later use. Aliquots of the humanized library were plated and single colonies transferred to 96 well plates. Each plate also contained 3 wells with positive control (BAP010_1) and negative control (vector only). Cultures were grown over night and plasmid DNA was prepped for transfection. CHO s cells were seeded in 96 well plates and transfected with miniprepped DNA of the humanized clones. Cell culture supernatant was collected 48 hours after transfection and IgG concentration was determined using BioAtla's ELISA protocol for quantification of human IgGs. Binding of the humanized clones to antigen NM9401 was tested in parallel using the antigen and protocol provided by NovelMed.

Specific activity (affinity/quant) was calculated for each clone and compared to the average specific activity of the positive control (BAP010_1) on the same plate. Clones with low expression levels (lower than BAP010_1) were then filtered out for selecting the primary hits. Low expression levels artificially inflate the specific activity and need to be avoided when selecting the hits. The top hits from each plate will be selected for confirmation.

Purification: The antibody was purified from 400 ml serum free cell culture supernatant using protein G columns Based on the ELISA data, fractions 4-6 (Peak 1, 1.5 ml) and fractions 3, 7-18 (Peak 2, 6.5 ml) were pooled. Half of each pool fractions was concentrated using Milipore spin columns (MWCO 50,000 Da).

Primary screen of humanized constructs: Aliquots of the humanized library were plated and single colonies transferred to 96 well plates. Each plate also contained 3 wells with positive control (BAP010_1) and negative control (vector only). Cultures were grown over night and plasmid DNA was prepped for transfection. CHO s cells were seeded in 96 well plates and transfected with miniprepped DNA of the humanized clones.

Specific activity (affinity/quant) was calculated for each clone and compared to the average specific activity of the positive control (BAP010_1) on the same plate. Clones with low expression levels (lower than BAP010_1) were then filtered out for selecting the primary hits. Low expression levels artificially inflate the specific activity and need to be avoided when selecting the hits. The top hits from each plate was selected for confirmation.

Example 1

Anti-Properdin IgG and F(ab')2 Bind Human Properdin with High Affinity

The affinity of anti-properdin IgG and F(ab)$_2$ to human properdin is in the low pM range. The antibody and its fragments bind properdin with similar affinities.

Figure 2:
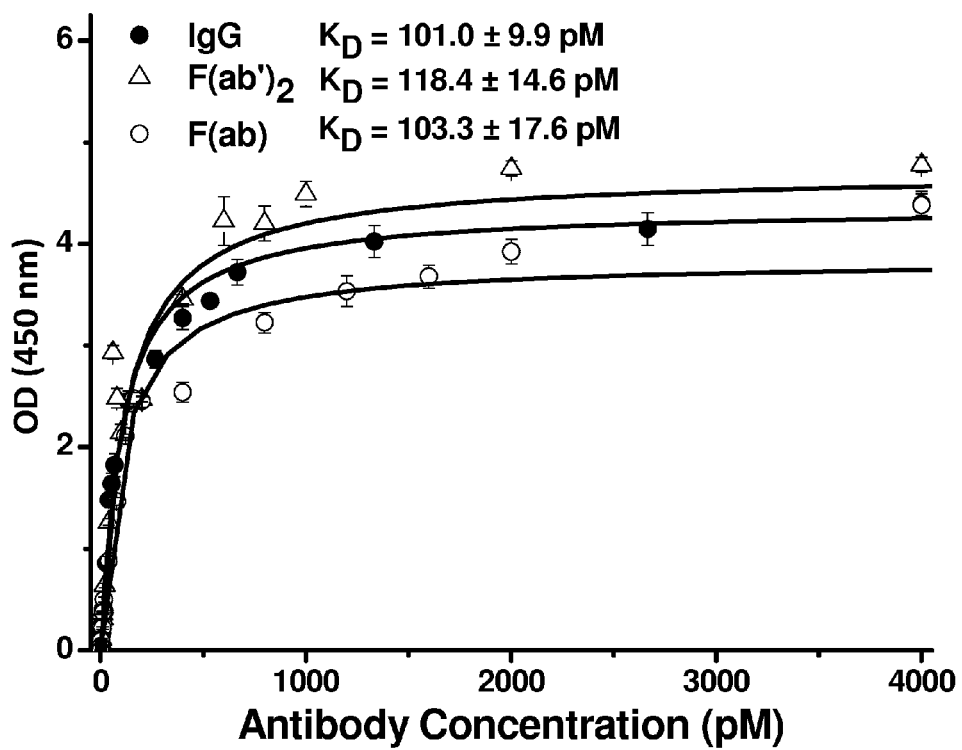
FIG. 2 shows the binding of an anti-properdin antibody IgG, Fab2, and Fab to properdin.

Polystyrene microtiter plates were coated with human properdin in phosphate buffered saline (PBS) overnight at 4° C. After aspirating the properdin solution, the wells were blocked with PBS containing bovine serum albumin (BSA) for 1 hour at room temperature. Wells without properdin coating served as background controls. Aliquots of monoclonal anti-properdin antibody IgG, F(ab')$_2$, and Fab were added to the properdin coated wells and allowed to incubate for 1 hour to allow for the binding of antibody and its fragments. Following a 1 hour incubation at room temperature, the plates were washed five times with PBS and incubated with a 1:2000 diluted detection peroxidase-conjugated goat anti-mouse monoclonal antibody. Following this incubation, the plates were rinsed and the bound peroxidase was identified using a TMB reagent. As shown in FIG. 2, NM9401-IgG, NM9401-F(ab')$_2$, and NM9401-Fab bind properdin with high affinity.

Example 2

Figure 3:
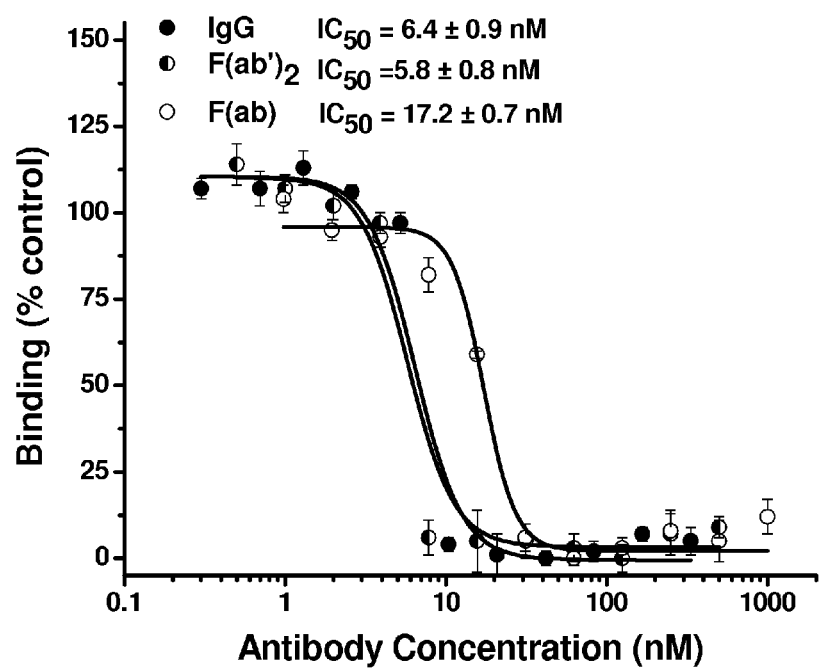
FIG. 3 shows that an anti-properdin monoclonal antibody inhibits AP activation as measured by the inhibition of rabbit erythrocyte lysis.

Anti-Properdin IgG, F(ab')$_2$, and Fab Inhibit Alternative Pathway (AP) Dependent Rabbit Red Blood Cell (rRBC) Lysis This erythrocyte lysis assay is based on the formation of a terminal complement-complex on the surface of the rRBC. As a result of the formation of this complex, the rRBCs are lysed. The progressive decrease in light scatter at 700 nm is a direct measure of erythrocyte lysis. rRBC(s) were incubated in normal human serum in gelatin veronal buffer containing 5 mM MgCl$_2$ (AP buffer). Under these conditions, the surface of rRBC triggers the activation of the alternative pathway in normal human serum. The alternative pathway activation leads to the formation of C5b-9 complex on the surface of the rRBC(s). Agents that inhibit the formation of C5b-9 complexes are expected to inhibit cellular lysis. To evaluate the effect of anti-properdin antibody and fragments thereof, various concentrations of IgG, F(ab')$_2$, and Fab were incubated with normal human serum (10% NHS) in AP buffer at 37° C. with a fixed concentration of rabbit erythrocytes. The rRBC lysis was evaluated with a temperature controlled ELISA plate reader capable of reading at 700 nm. A progressive decrease in light scatter (due to the lysis of intact cells) was measured at 700 nm as a function of time. The data were recorded and analyzed with a SpectraMax 190 plate reader and SoftMax software. For the calculation, the total inhibition was calculated at each concentration of the IgG, F(ab')2, and Fab and the results were expressed as a % of unlisted controls. Data at each concentration was plotted in a sigmoid plot with MicroCal Origin Software. As shown in FIG. 3, IgG and fragments of IgG inhibit AP dependent hemolysis of rRBC in normal human serum with an IC$_{50}$ of approximately 5.8 and 17.2 nM.

Example 3

Figure 4:
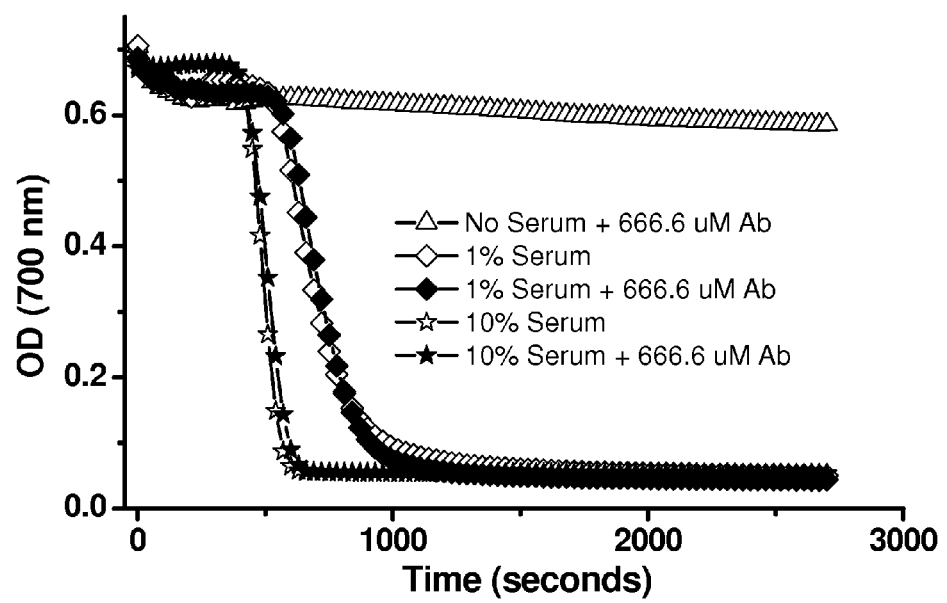
FIG. 4 shows that an anti-properdin monoclonal antibody does not inhibit classical pathway activation in 1% and 10% normal human serum in buffer.

Anti-Properdin Monoclonal Antibodies do not Inhibit Classical Pathway Activation Monoclonal antibodies of the present invention do not inhibit the classical pathway required for host defense. Antibody sensitized sheep erythrocytes were incubated with 1% or 10% normal human serum in gelatin veronal buffer containing calcium (5 mM CaCl$_2$/MgCl$_2$) buffer (CP buffer). Antibody sensitized sheep cells activate the classical pathway. As a result, C5b-9 is formed on the surface of the erythrocyte resulting in the lysis of the erythrocytes. We tested 1% and 10% normal human serum. Under both conditions, NM9401 inhibited erythrocyte lysis. In a typical assay, erythrocytes were incubated in 1%/10% normal human serum in CP buffer to allow complement activation to occur. As a result of CP activation, C5b-9 is formed on the surface of erythrocytes causing cellular lysis. The progressive decrease in light scattering due to cellular lysis is measured at 700 nm as a function of time. As shown in FIG. 4, NM9401 IgG does not inhibit the lysis of the antibody sensitized sheep cells at both serum concentrations. No serum control showed negligible effect. These results suggest that the anti-properdin antibodies are capable of selectively inhibiting the alternative complement pathway without affecting the classical pathway activation.

Example 4

Figure 5:
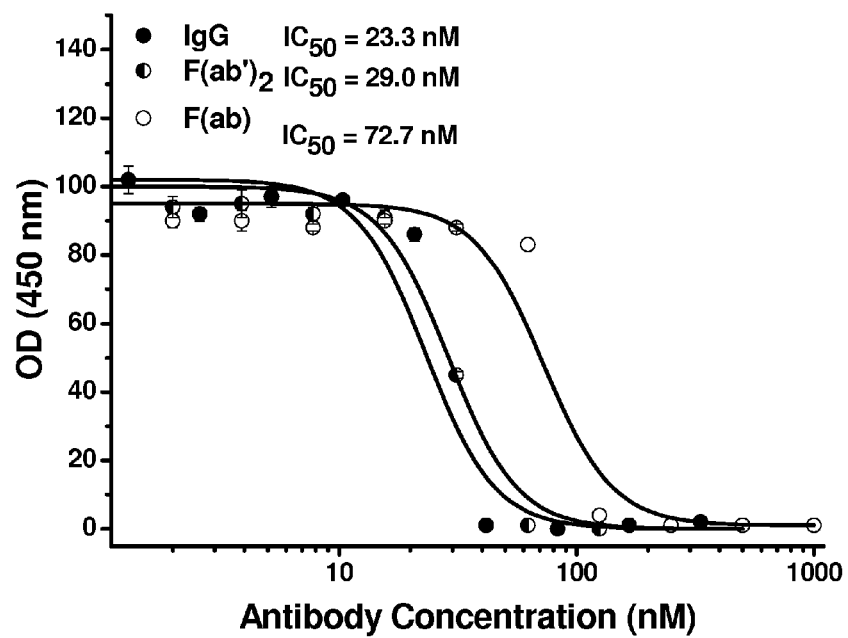
FIG. 5 shows that anti-properdin antibody IgG, Fab2, and Fab inhibit the binding of properdin to C3b with high affinity.

The Anti-Properdin Antibody of the Present Invention Inhibits the Binding of Properdin to C3b Properdin binds C3b with high affinity. The anti-properdin antibody of the present invention, at various concentrations in a solution containing a fixed concentration of properdin (50 nM), was incubated in wells that had been coated with C3b. This experiment was set up to evaluate whether anti-properdin antibody would inhibit properdin binding to C3b. As shown in FIG. 5, NM9401 inhibits properdin binding to C3b with 29 nM for Fab2 and 72 nM for Fab, suggesting the molar ratio of antibody to properdin is in the range of 0.5 to about 1.2.

Example 5

Antibodies Binding to the Same Epitope Compete to be Bound to the Epitope

Figure 6:
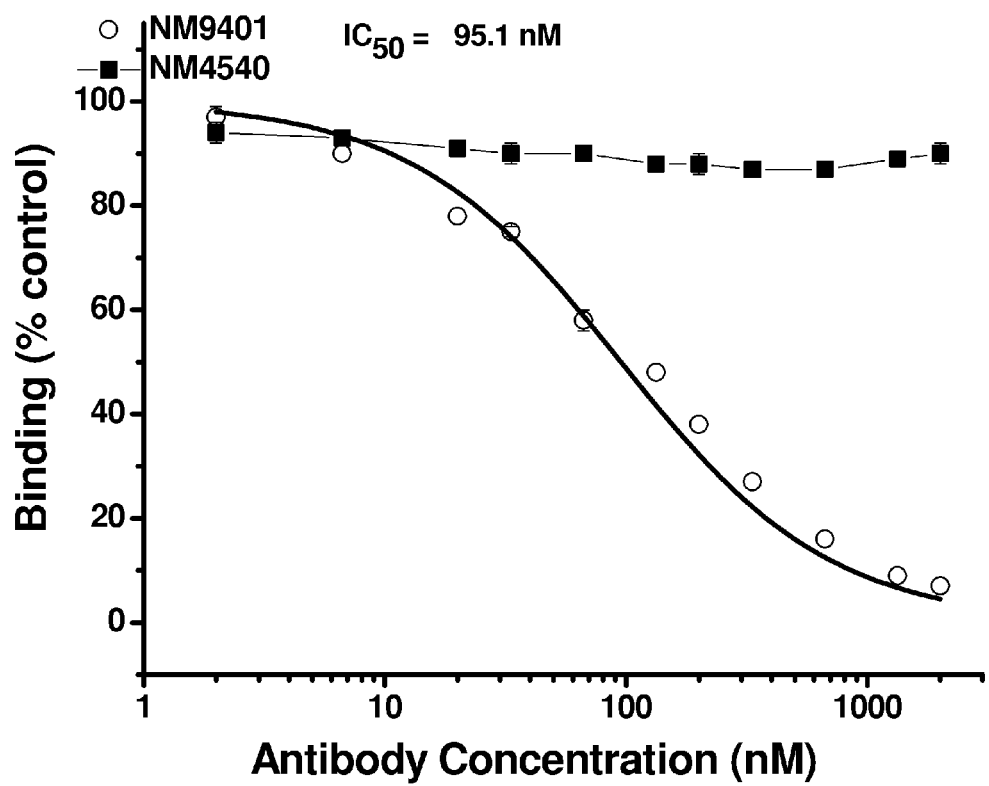
FIG. 6 shows that anti-properdin antibody IgG and NM4540 do not compete for binding to properdin.

Polystyrene microtiter well plates were coated with properdin. The wells were incubated with 50 nM concentration of the anti-properdin biotinylated intact antibody to generate a saturation curve. Biotinylated antibody at a fixed concentration was incubated with varying concentrations of unlabeled antibody assigned an ATCC number (PTA-10649). The inhibition curve was generated by detecting the biotinylated antibody using HRPO-neutavidin conjugate. These studies suggest that antibodies that bind the specific epitope on properdin do not compete for the same binding site on properdin. The data is shown in FIG. 6.

Example 6

Anti-Properdin IgG, Fab'2, and Fab Inhibit the Formation and Deposition of C3b

Figure 7:
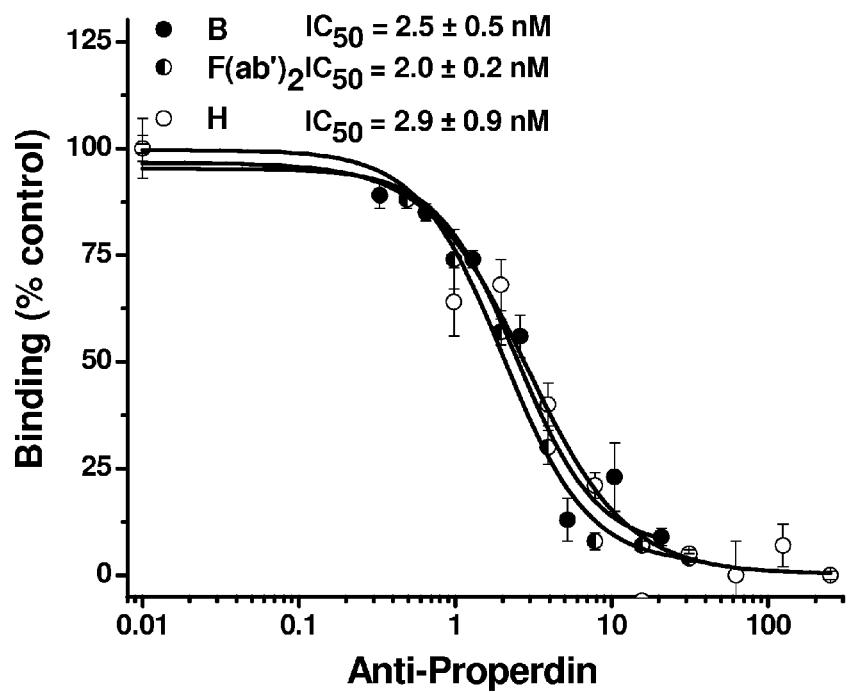
FIG. 7 shows that anti-properdin antibody IgG, Fab2, and Fab inhibit the formation of C3b in an assay.
Figure 8:
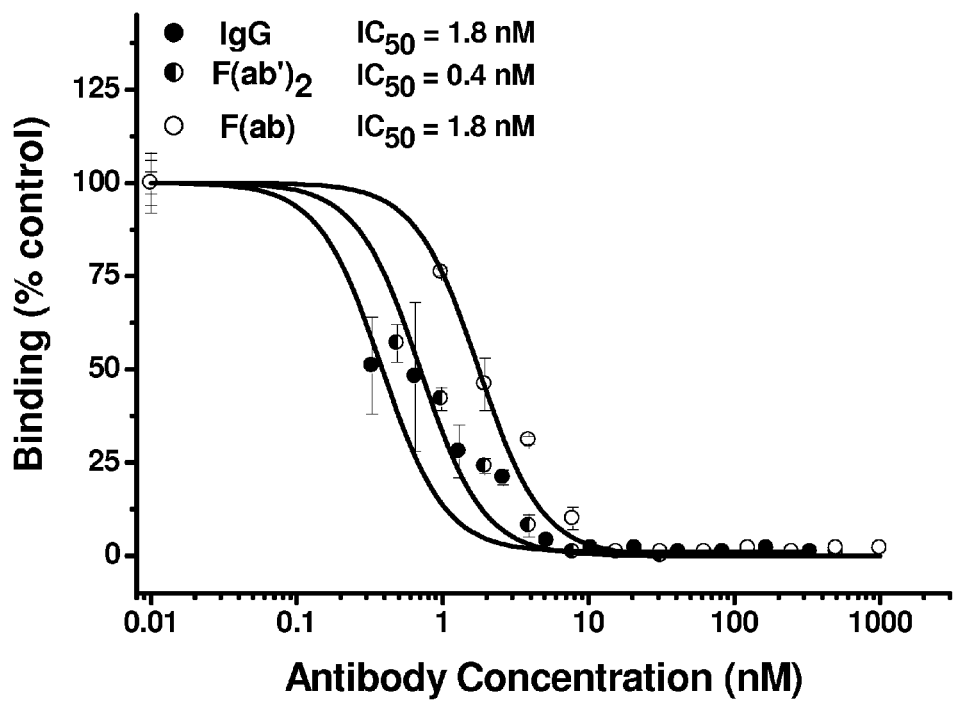
FIG. 8 shows that anti-properdin antibody IgG, Fab2, and Fab inhibit the formation of PC3b in the same assay as shown in FIG. 7.
Figure 9:
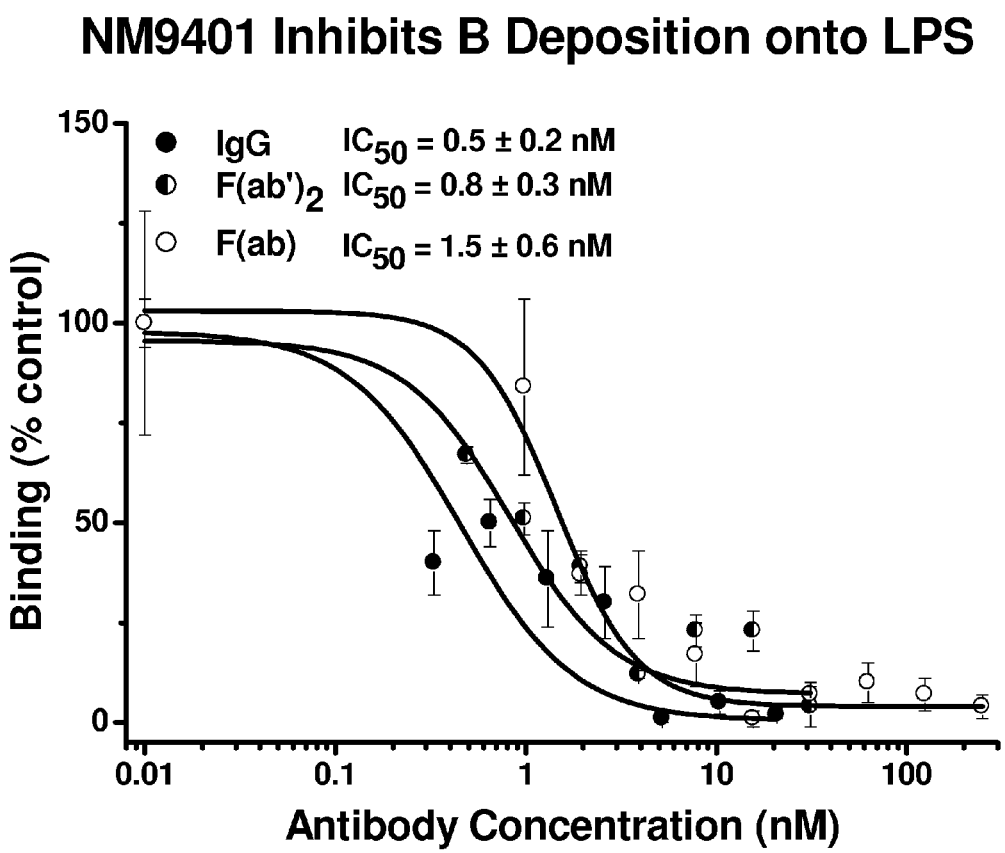
FIG. 9 shows that anti-properdin antibody IgG, Fab2, and Fab inhibit the formation of PC3bBb in the same assay as shown in FIG. 7.

AP activation generates C3a and C3b as a result of C3 cleavage by the C3 convertase of the alternative complement pathway. Alternative complement pathway is activated in normal human serum by lip polysaccharide from *Salmonella* Typhosa under conditions that allow the activation of the alternative complement pathway. We have utilized this assay to demonstrate whether anti-properdin antibody of this invention would inhibit the formation and deposition of C3b. Deposition of C3b initiates the start of the alternative complement pathway. As a way of mechanism, activated and deposited C3b provides high affinity binding to properdin. Properdin-C3b complexes bind factor B and the complex is cleaved by factor D to generate PC3bBb, an alternative pathway C3 convertase. As the alternative pathway proceeds, C5b-9 complexes are formed and deposited. As shown in FIGS. 7, 8, and 9, the formation and deposition of C3b is inhibited. Because C3b formation and deposition is inhibited, the deposition of other components, such as properdin, factor Bb, and C5b-9, is also inhibited.

In a typical assay, polystyrene microtiter plate wells were coated with LPS (Lip polysaccharide from *Salmonella* Typhosa) at 2 μg/50 μl in PBS overnight. The wells were incubated with BSA in PBS to block the unoccupied sites in the wells. Following a 2-hour blocking at room temperature and rinsing with PBS, normal human serum (10%) in AP buffer was mixed with varying concentrations of the anti-properdin antibody and derived fragments. The mixture was incubated onto LPS coated wells. The plate was incubated for 2 hours at 37° C. to allow complement AP activation to occur. Following incubation, the plates were extensively washed with PBS, and components of the C3 convertase were detected with the appropriate antibodies. We detected C3b with rabbit anti-human C3c at 1:2000 in blocking solution, properdin was detected with goat anti-human P, Bb was detected with goat anti-human factor Bb at 1:500 in blocking solution and C5b-9 was detected with HRPO-conjugated neo-anti-human C5b-9 at 1:2000 in blocking solution. Plates were incubated with their respective antibodies for 1-hour at room temperature. Following the incubation, the plates were rinsed with PBS and the bound antibodies were detected with peroxidase labeled goat anti-rabbit at 1:2000 for C3b and peroxidase labeled rabbit anti-goat at 1:2000 in blocking solution for P detection. All plates were developed with TMB following extensive washing with PBS. The blue color was quenched with 1 M orthophosphoric acid. The presence of C3b, P and Bb and MAC together are indicative of AP C3 convertase formation. The antibodies of the present invention are shown to inhibit C3b formation and therefore deposition (FIG. 7), PC3b deposition (FIG. 8), and PC3bBb deposition (FIG. 9). This data provides direct evidence that anti-properdin monoclonal antibodies prevent C3 convertase formation and thus AP activation.

Example 7

NM9405 Inhibits Platelet Dysfunction in Pig Whole Blood Tubing Loop Model

Figure 10:
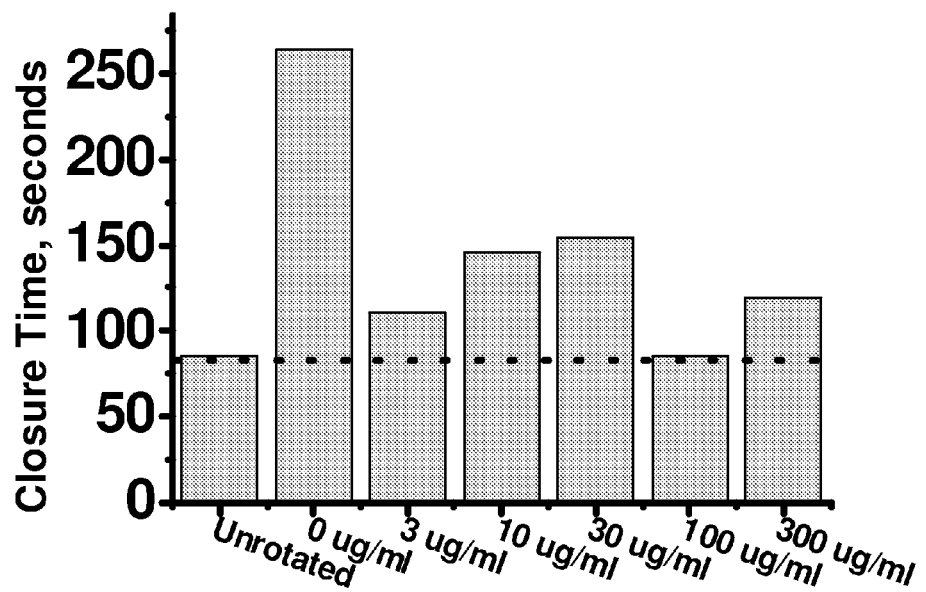
FIG. 10 shows that an anti-properdin antibody inhibits platelet dysfunction in pigs in a whole blood model of cardiopulmonary bypass.

Loss of platelet function occurred when platelets were activated. Activated platelets tend to aggregate with leukocytes and get removed from circulation causing thrombocytopenia. Platelet dysfunction results from activated platelets. Measurement of closure time is a good indication for platelet function. Closure time is defined as the time it takes platelets to aggregate and block the aperture in the membrane. Whole blood (0.8 ml) was transferred into the reservoir of the test cartridge. The blood was warmed to 37° C., and drawn under vacuum through a 200 μm stainless steel capillary and a 150 μm aperture in a nitrocellulose membrane coated with collagen. As the blood moves through the capillary, it comes in contact with the collagen coated membrane. The collagen induced formation of the platelet plug that blocks blood flow through the aperture. The time taken to occlude the aperture is reported as the closure time. In this process, platelets initially adhere to collagen coating in the membrane resulting in aggregation. Prolonged closure time is indicative of platelet dysfunction. Following the tubing loop model of extracorporeal circulation pig blood was evaluated for AP activity (not shown) and platelet function. Aliquots of whole pig blood (0.8 ml) were transferred into the reservoir of the disposable test cartridge from Dade Behring. The blood was warmed to 37° C., and drawn, by vacuum, through a 200 μm stainless steel capillary and a 150 μm aperture in a nitrocellulose membrane coated with collagen. Closure times were recorded for each sample and plotted. As the experiment requires large volumes of blood, only a few loops were tested. As shown in FIG. 10, the rotated samples display a three-fold increase in the closure time in a 2 h circulation period. NM9401-F(ab')$_2$-treated blood samples, show inhibition of platelet dysfunction.

Example 8

Figure 11:
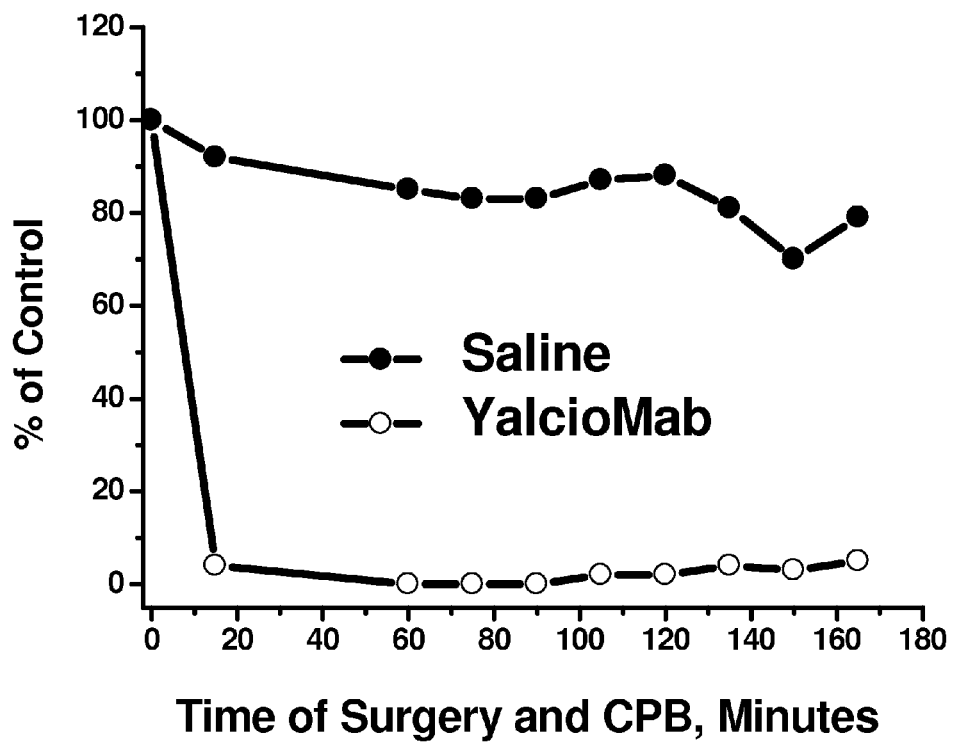
FIG. 11 shows that an anti-properdin antibody inhibits AP Activation in vivo in pigs undergoing cardiopulmonary bypass.

NM9401-F(ab')$_2$ Inhibits AP Activation in Pigs Undergoing Cardiopulmonary Bypass Although NM9401-F(ab')$_2$ inhibits AP activation, cellular activation in whole blood, TNF-α and Elastase, and platelet dysfunction, it was to be determined whether such studies will translate in vivo to pigs undergoing cardiopulmonary bypass. This pig study was conducted under an IACUC approved protocol. In this non-survival open chest CPB study, two female pigs (30 Kg weight) were subjected to open chest CPB with one treated and one control. Both animals were sedated and intubated prior to the surgical procedure. Both received clinical doses of heparin consistent with standard CPB surgical procedures. Vital signs such as temperature, pCO$_2$, pO$_2$, pH, blood calcium and EKG were monitored throughout the study to ensure that the pigs were stable. Albumin was given as needed to both pigs. Body temperature, blood pressure, and heart and pulse rate were also maintained. The CPB circuits of 400 ml capacity were used along with a plasmalyte for priming the circuit. During the course of the surgery and bypass, blood samples (3.0 mls) were collected at the pre-surgery, post sternotomy, and during the bypass at various time points: 0, 15, 30, 75, 90, 105, 120, 135, 150 and 165 minutes. One pig received NM9401-F(ab') and the other one received the vehicle (Saline). A single bolus dose of NM9401-F(ab') at 3 mg/Kg body weight was administered i.v. and the effect on AP activation, properdin levels, platelet dysfunction and blood loss were evaluated. AP complement activity was measured in plasma samples drawn at regular time intervals. We utilized the erythrocyte lysis assay to measure C5b-9. NM9401-F(ab') treated pigs showed inhibition of alternative pathway activation throughout the duration of the CPB. NM9401-F(ab') neutralizes properdin in pigs undergoing bypass—Properdin binds C3b and C5 and initiates the AP activation via convertase assembly. NM9401-F(ab')$_2$ binds properdin at its active site and blocks its function. As a result, AP activation does not occur. As shown in FIG. 11 NM9401-F(ab')$_2$ inhibits AP activation as measured by the total properdin remaining in serum.

Figure 12:
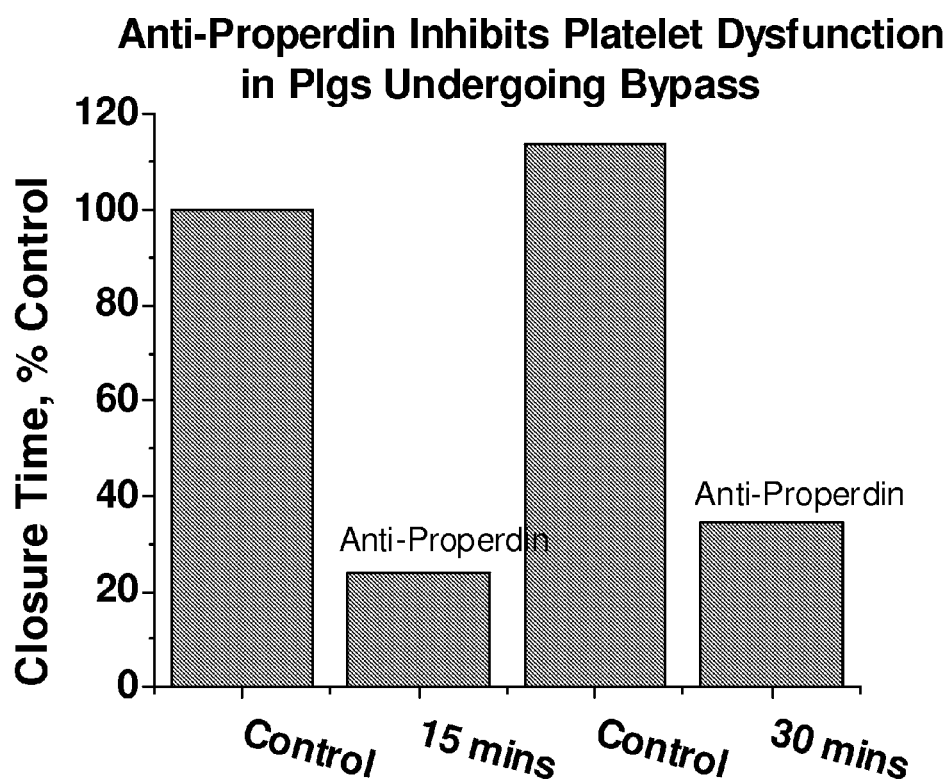
FIG. 12 shows that an anti-properdin antibody inhibits platelet dysfunction in pigs undergoing cardiopulmonary bypass.

Platelet dysfunction is one of the major hallmarks of bleeding complications. During the CPB procedure, platelets are activated, activated platelets aggregate, leukocyte-platelet aggregates are removed from circulation causing thrombocytopenia. Platelets express C3a receptors that when occupied by C3a produced during complement activation causes platelets to become dysfunctional. Dysfunctional platelets show an increase in the closure time because they lose the ability to clot in response to collagen. Thus, platelet dysfunction is measured by PFA-100. Saline treated pigs demonstrate closure times much higher than NM9401-F(ab')$_2$ treated pigs. These data are consistent with the data we outlined above in which NM9401-F(ab')$_2$ prevented platelet dysfunction in isolated blood undergoing extracorporeal circulation. Blood loss, as measured by the total volume of blood collected in the suction system reservoir during CPB, is reduced significantly in NM9401-F(ab')$_2$ treated pigs. These data suggest the importance of NM9401-F(ab')$_2$ for reducing complications of the CPB. Reduction in blood-loss is a significant finding as it has clinical implications and costs of surgery per patient in a clinical setting. Excessive blood loss is reported in patients undergoing bypass. We measured the total blood loss in both pigs undergoing CPB. Pigs treated with NM9401-F(ab')$_2$ demonstrated a total of 67% reduction in blood loss as compared to the untreated controls. Platelet dysfunction was also prevented, as shown in FIG. 12.

Example 9

NM9405 Inhibits Myocardial Ischemia Reperfusion Injury in Rabbits

This study evaluated the effect of single bolus dose of NM9401-F(ab')$_2$ in twelve rabbits with six treated and six controls. The study used a 30 minutes of ischemia followed by 2 hours of reperfusion. As shown in FIG. 13, the treated group showed a decrease in the infarct size in six animals (right panel) as compared to control group (left panel). The procedure for generating infarction and tetra-zolimum staining used methods and procedures. These preliminary data show that NM9401-F(ab')$_2$ treated animals had a smaller infarct than control animals. The colored two-panel figure is taken from control infracted heart and NM9401-F(ab')$_2$ treated heart. The heart sections after the procedure were sliced and stained with tetrazolium (TTC). In the experiment, at the end of reperfusion, the coronary artery was re-occluded and fluorescent polymer microspheres were infused into the perfusate to demarcate the ischemic zone (area at risk) as the area of tissue without fluorescence. The heart was weighed, frozen and cut into 2 mm thick slices. The slices were incubated with 1% TTC (tetrazolium staining) in PBS at 37° C. for 10-12 minutes. TTC stains non-infarcted myocardium brick red. The slices were then fixed in 10% formalin to preserve the stained (viable) and unstained (necrotic) tissue. The risk zone was identified by illuminating the slices with UV light. The areas of infarct and risk zone were determined by planimetry of each slice and the volumes were calculated by multiplying each area by the slice thickness and summing them for each heart.

Example 10

NM9401-F(ab)$_2$ Inhibits Choroidal Neo Vascularization in Rabbits

Figure 14:
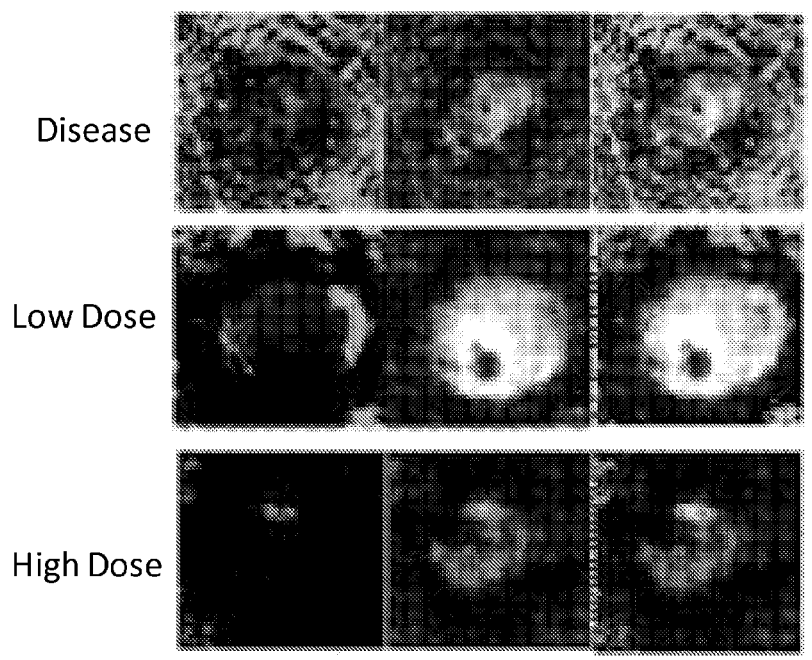
FIG. 14 shows that an anti-properdin antibody inhibits CNV in rabbits undergoing macular degeneration.

Choroidal Neovascularization (CNV) can be induced by laser treatment in a rabbit eye. This model resembles, in many ways, the wet AMD model. Twelve healthy rabbits (mean body weight, about 2.5-4.0 kg) were used in the study. All the animals received humane care according to the Guide for the Care and Use of Laboratory Animals of the National Research Council (National Academy Press, revised 1996). The rabbits were anesthetized with a mixture (4:1) of ketamine hydrochloride (24 mg/kg) and xylazine hydrochloride (6 mg/kg). The pupils were dilated with 1% tropicamide and 2.5% phenylephrine hydrochloride eye drops. Krypton red laser photocoagulation (50-µm spot size, 0.05-s duration, 250 mW) was used to generate multiple laser spots in each eye surrounding the optic nerve by using a hand-held cover slip as a contact lens. A bubble formed at a laser spot indicated a rupture of the Bruch's membrane. The laser spots were evaluated for the presence of CNV on day 28 after laser treatment, using confocal microscopy. After anesthesia and dilation of the pupil, the anterior chamber was entered via the limbus with a 28-gauge needle to decompress the eye. Under an operating microscope, which allowed visualization of the retina, a 32-gauge (blunt) needle was passed through a scleral incision, just behind the limbus, into the vitreous cavity or subretinal space. A Hamilton syringe was used to inject the NM9401-F(ab')$_2$. At the time of euthanasia, rabbits were anesthetized with an overdose of ketamine/xylazine mixture (4:1) and perfused through the heart with 1 ml PBS containing 50 mg/ml fluorescein-labeled dextran (FITC-Dextran, 2 million average molecular weight, Sigma). The eyes were removed and fixed for 1 h in 10% phosphate-buffered formalin. The cornea and the lens were removed and the neurosensory retina was carefully dissected from the eyecup. Five radial cuts were made from the edge of the eyecup to the equator; the sclera-choroid-retinal pigment epithelium (RPE) complex was flat-mounted, with the sclera facing down, on a glass slide in aquamount. Flat mounts were stained and examined with a confocal microscope (Zeiss LSM510). The CNV will stain green whereas the elastin in the Bruch's membrane will stain red. A laser spot with green vessels will be scored as CNV-positive, and a laser spot lacking green vessels will be scored as CNV-negative. Twenty-eight days after laser treatment, all animals were perfused with 1 ml of PBS containing 50 mg/ml fluorescein-labeled dextran (FITC-dextran; average molecular mass, 2×10$^6$; Sigma-Aldrich) and sacrificed. The eyes were harvested and fixed in 10% phosphate-buffered formalin, and retinal pigment epithelium (RPE)-choroid-scleral flat mounts were prepared as previously described. The green color in the laser spots is the CNV complex. If the CNV was found to be <3% of the total laser spot area, it was graded as negative while CNV >3% was considered positive. As shown in FIG. 14, a single bolus prophylactic dose of NM9401 reduces CNV in rabbits over a 28-day period.

Example 11

Figure 15:
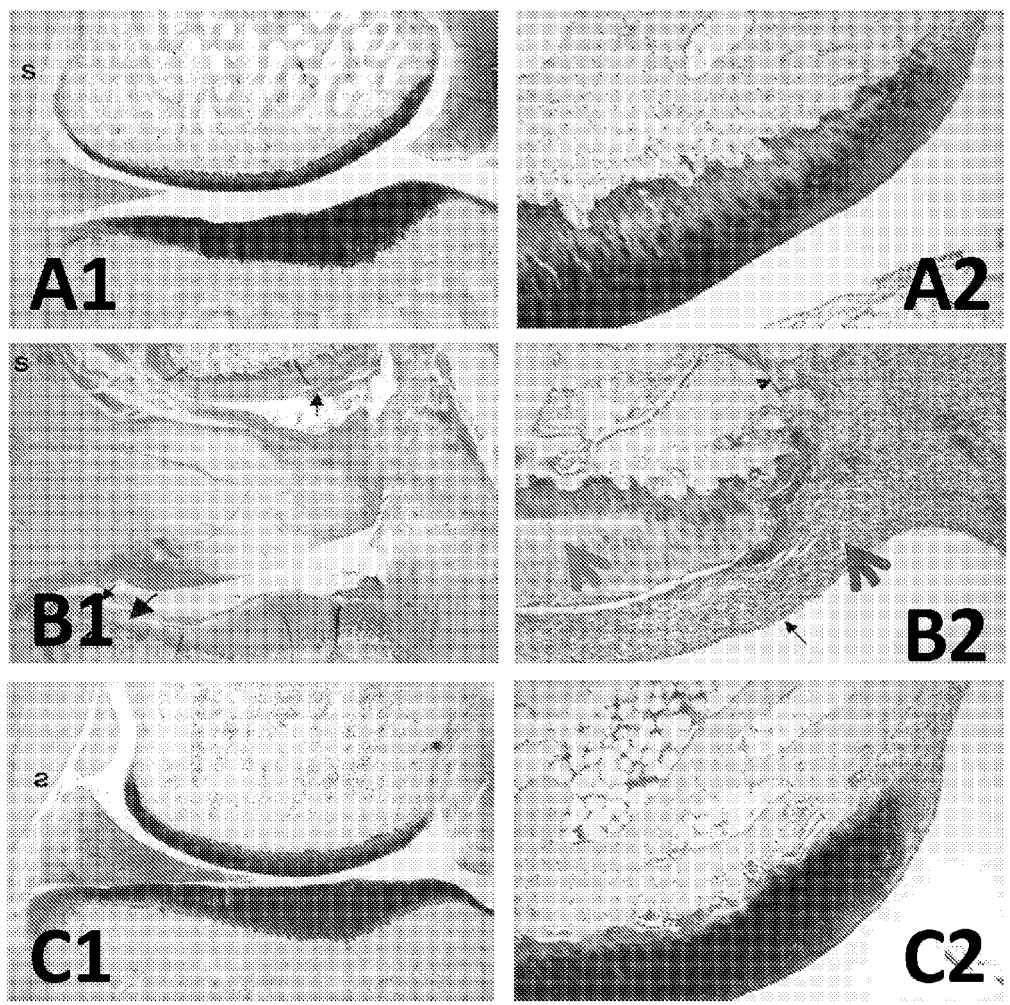
FIG. 15 shows that an anti-properdin antibody inhibits joint inflammation in a rabbit model of rheumatoid arthritis.

NM9401-Fab2 Inhibits Joint Destruction in Rheumatoid Arthritis in Rabbits Treated with a Single Prophylactic Dose Arthritis was induced in rabbits using published procedures known in literature. Animals were given a single bolus dose via intra-articular, intravenous, intraperitoneal, or subcutaneous procedure. Animals were sacrificed at 28 day. Limbs were subjected to radiographs, CT scans and histological evaluations. The NM9401-Fab2 treated animals at 200 µg/knee joint prevent joint damage. These data, as shown in FIG. 15, show that NM9401-Fab2 provides tissue, cartilage and bone protection from arthritis damage.

Example 12

Sequencing of Murine Monoclonal Antibody

Hybridoma secreting NM9401-IgG1 were pelleted and the total RNA was isolated. cDNA was synthesized using oligo dT primers and Reverse transcriptase. Kappa light chain variable domains were amplified from the cDNA using a set of mouse specific kappa primers. The forward primers were designed to amplify the mouse light chain variable domains in combination with a kappa specific reverse primer. Seven different primer combinations (mK2, mK3, mK7, mK8, mK9, mk10, mK11) resulted in a PCR product of the expected size. PCR products were gel purified, TOPO-TA cloned and sequenced (4 clones each). Sequence analysis revealed that primer combinations mK2, mK3, mK7, mK8, mK9, and mK11 amplified the same light chain sequence (with only minor variations based on primer ambiguities). These clones have a stop codon in the CDR3/Framework 4 region yielding a non productive V-J rearrangement. Sequence analysis of the clones derived with primer combination mk10 showed that a single light chain was amplified. In order to verify the N-terminus of the obtained sequence, an additional PCR reaction was performed with a forward primer annealing to the secretion signal and a reverse primer specific for the CDR3 in clone mK10. The exact same DNA sequence was obtained with the second primer set. Heavy chain variable domains were also amplified in a similar manner from cDNA using a specific set of mouse specific heavy chain primers. The forward primers are designed to amplify the mouse heavy chain variable domains in combination with an IgG1/2 specific reverse primer. Five different primer combinations (mH1, mH2, mH4, mH5, and mH6) resulted in a PCR product of the expected size. PCR products were gel purified, TOPO-TA cloned and sequenced (4 clones each). Sequence analysis revealed that primer mH2 amplified only non-antibody specific mouse transcripts. Primer combinations mH4 and mH5 amplified the same transcript.

Primer combinations mH1 and mH6 resulted in 3 clones with slight amino acid variations. Three amino acid differences in framework 1 (aa positions 7 to 9) are due to primer sequences. The amino acid change at position 64 is probably caused by a PCR error. A BLAST search against the mouse genome was performed in order to identify the corresponding germline V region gene. Mouse germline gene IgH1-4 was identified as the closest match (89% identity). An additional PCR reaction was performed with a forward primer specific for the N-terminus of the germline gene IgH1-4 and a reverse primer specific for CDR H3 identified in the previous steps. The resulting PCR product was TOPO-TA cloned and 10 clones were sequenced. All clones had the exact same sequence. CDR-H1, CDR-H2, and CDR-H3 are the three CDR sequences within the variable region of the antibody. Heavy chain sequences are shown in FIGS. 16, 24, 25, and 26. Correspondingly, light chain sequences are shown in FIGS. 17, 21, 22, and 23. The epitope mapping sequence is shown in FIG. 29.

Example 13

Purified Recombinant Antibody BAP010 1 was Tested for Binding to the Antigen Properdin The calculated Kd value is in good correlation with the Kd of the original mouse antibody. The recombinant antibody was also tested in a hemolysis assay. In this assay, no activity could be detected. The chimeric antibody was purified from 400 ml serum free cell culture supernatant. Cell culture supernatant was loaded on the protein G column (equilibrated in 10 mM Na$_2$HPO$_4$/NaH$_2$PO$_4$, pH 7.0). The column was washed with 20 CV of binding buffer. Bound protein was eluted with a step gradient (elution buffer: 12.5 mM Citric Acid, pH 2.7). 0.5 ml fractions were collected and immediately neutralized (50 ul, 0.5 M Na$_2$HPO$_4$/NaH$_2$PO$_4$, pH 8.0). The amount of recombinant IgG in the individual fractions from the protein G column was determined using a standard ELISA protocol with anti-human IgG conjugated to HRP as the secondary antibody and purified human IgG.

Figure 18:
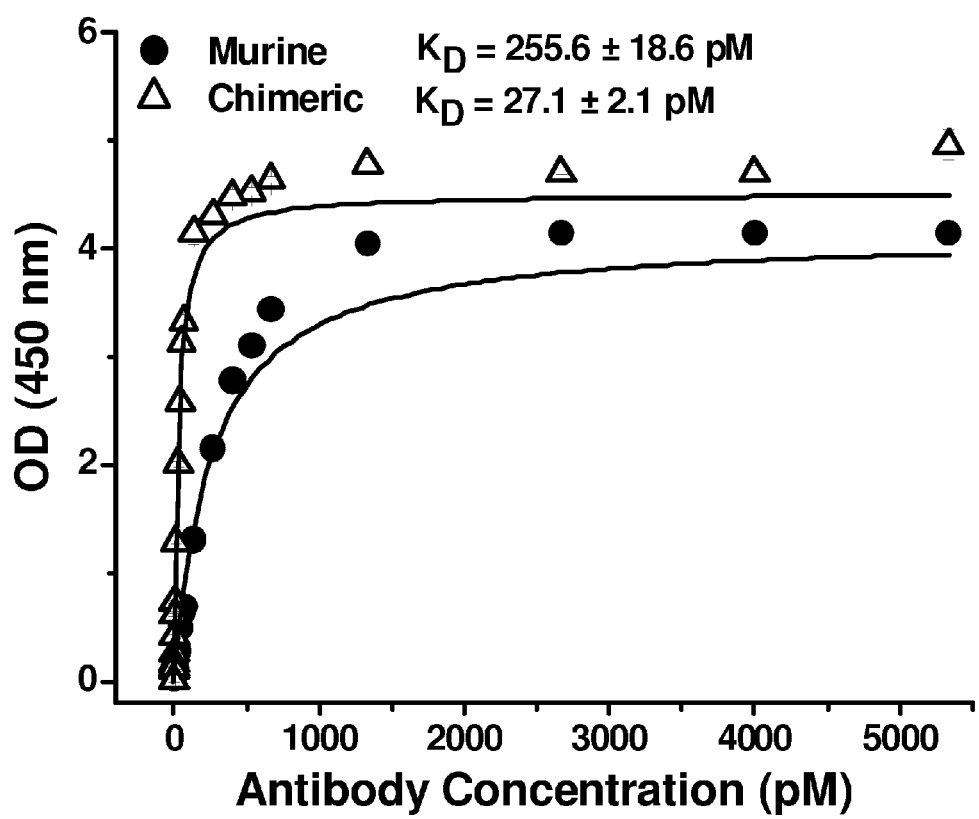
FIG. 18 shows the binding affinity of the anti-properdin IgG antibody and the anti-properdin antibody chimeric IgG antibody to properdin.

Binding affinity of the chimeric anti-properdin monoclonal antibody and NM9401-IgG appear to be comparable, as expected. This is shown in FIG. 18.

Figure 19:
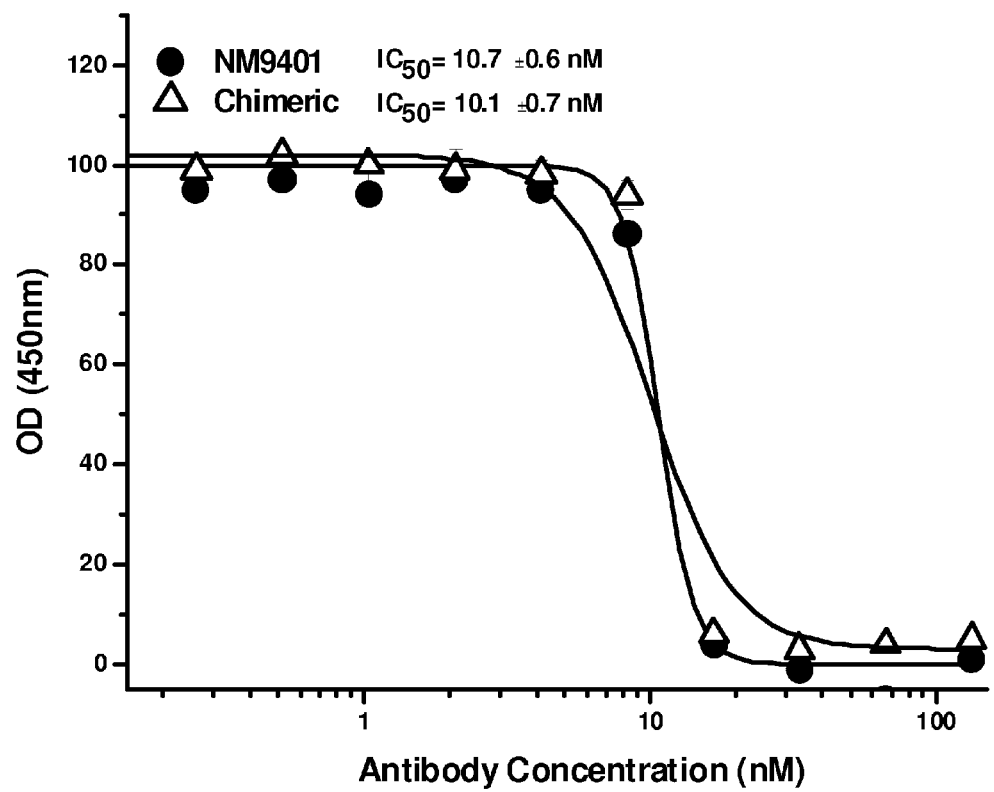
FIG. 19 shows that the humanized anti-properdin antibody and the chimeric anti-properdin antibody inhibit the binding of properdin to C3b.

The inhibition of properdin binding to C3b by both murine and chimeric anti-properdin monoclonal antibodies appear to be comparable as indicated by FIG. 19.

Figure 20:
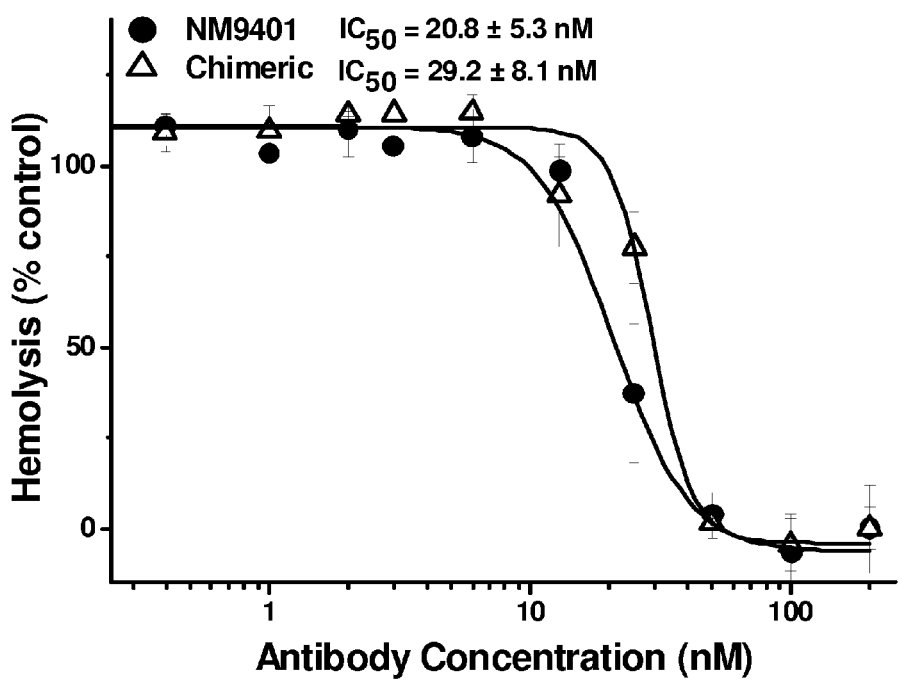
FIG. 20 shows that the humanized IgG antibody and the chimeric anti-properdin IgG inhibit the hemolysis of rRBC in 10% normal human serum.

Both monoclonal antibodies were also evaluated in an erythrocyte lysis assay using rabbit erythrocytes as target cells for MAC lysis. Both NM9401-IgG and chimeric monoclonal BAP010_1 appear to be comparable with IC50 values of inhibition being around 20-30 nM as shown in FIG. 20.

Example 14

Figure 27:
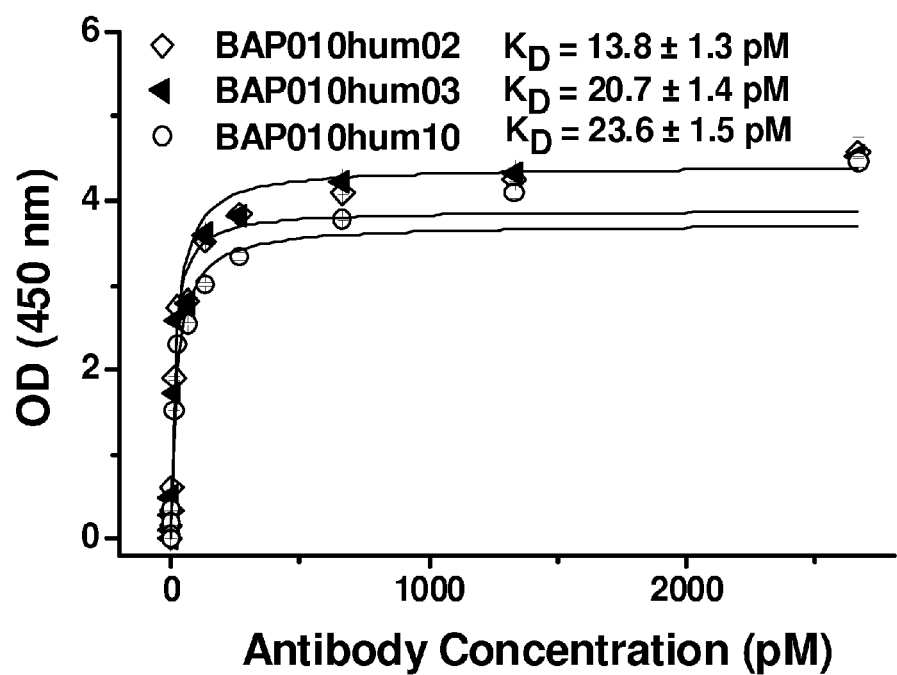
FIG. 27 shows the binding affinities of three selected humanized monoclonal antibodies SEQ ID NOs: 36, 37, and 44.
Figure 28:
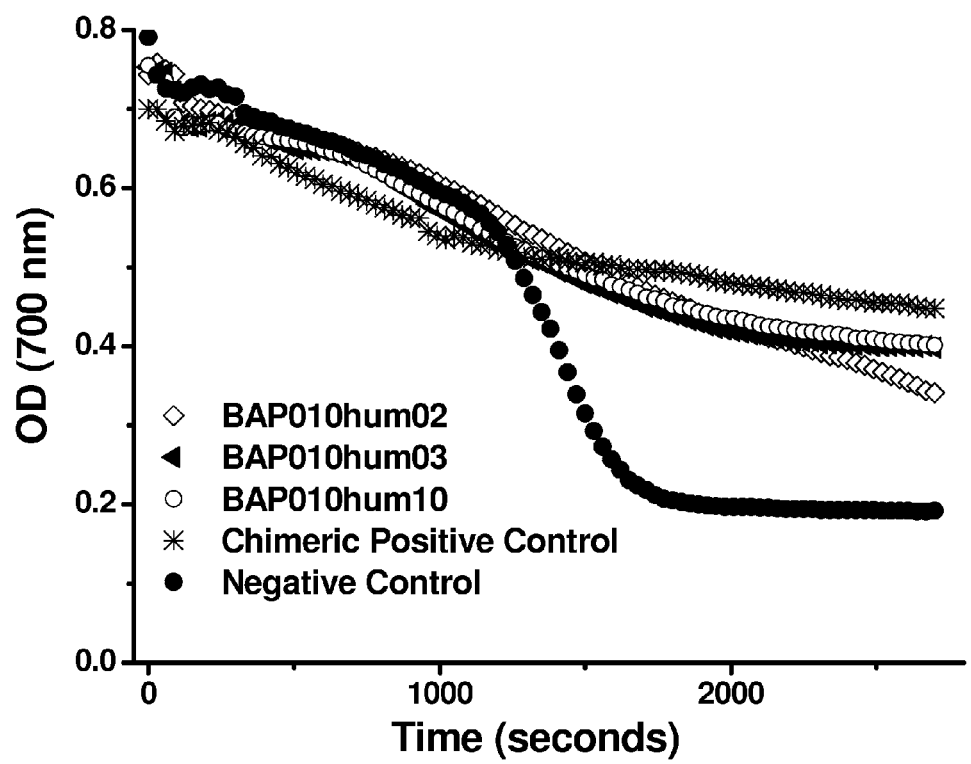
FIG. 28 shows that the three selected humanized monoclonal antibodies inhibit alternative complement pathway activation as shown by the inhibition of hemolytic activity in the AP buffer.

Binding and Functional Activity of Humanized Anti-properdin Monoclonal Antibodies Supernatants from each of the sixteen identified clones were concentrated, quantified and evaluated in a properdin ELISA to determine the binding constants, as shown in FIG. 40. The binding affinity ranged from 13 pM to 57 pM compared to the affinity of the chimeric gold standard BAP010_1 which was in the range of 54 pM. The affinity of the various clones appears to be higher than the original gold standard Kd=255 pM. Functional activity of each clone was evaluated at a given concentration. As shown in FIG. 41, all the clones inhibited alternative pathway activation with varying efficacy. Three clones were selected based on binding affinity and AP activation. These three clones were selected for further characterization. As shown:

SEQ ID NO 19>BAP010hum02_LC
SEQ ID NO 36>BAP010hum02_HC
SEQ ID NO 20>BAP010hum03_LC
SEQ ID NO 37>BAP010hum03_HC
SEQ ID NO 27>BAP010hum10_LC
SEQ ID NO 44>BAP010hum10_HC FIG. 27 shows the binding affinities of the three selected humanized monoclonal antibodies. Furthermore, FIG. 28 shows the results of the erythrocyte lysis assay demonstrating that all three are capable of inhibiting the alternative pathway activation in normal human serum.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. An isolated anti-properdin antibody or antigen binding portion thereof, comprising a heavy chain variable domain including the 3CDRs in SEQ ID NO: 1 and a light chain variable domain including the 3CDRS in SEQ ID NO: 9.

2. The anti-properdin antibody or antigen binding portion thereof of claim 1, comprising a heavy chain selected from the group consisting of SEQ ID NO: 1, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, and SEQ ID NO: 50.

3. The anti-properdin antibody or antigen-binding portion thereof of claim 1, comprising a light chain selected from the group consisting of SEQ ID NO: 9, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33.

4. The anti-properdin antibody or antigen binding portion thereof of claim 1, wherein the anti-properdin antibody or antigen binding portion thereof comprises a heavy chain variable domain having at least 90% sequence identity to the amino acid sequence of SEQ ID NO: 1.

5. The anti-properdin antibody or antigen binding portion thereof of claim 1, wherein the anti-properdin antibody or antigen binding portion thereof comprises a light chain variable domain having at least 90% sequence identity to the amino acid sequence of SEQ ID NO: 9.

6. The anti-properdin antibody or antigen binding portion thereof of claim 1, wherein the anti-properdin antibody comprises a heavy chain variable domain having at least 90% sequence identity to the amino acid sequence of SEQ ID NO: 1 and a light chain variable domain having at least 90% sequence identity to the amino acid sequence of SEQ ID NO: 9.

7. A method of inhibiting alternative complement pathway activation in a mammal, the method comprising the step of administering of an isolated anti-properdin antibody or antigen binding portion thereof of claim 1 to a human or other mammal.

8. The method of claim 7, wherein the mammal has a disease or disorder in which activation of the alternative complement pathway plays a role, and wherein the step of administering the antibody or antigen binding fragment thereof treats the disease or disorder.

* * * * *

UNITED STATES PATENT AND TRADEMARK OFFICE
CERTIFICATE OF CORRECTION

| | | |
|---|---|---|
| PATENT NO. | : 8,664,362 B2 | Page 1 of 1 |
| APPLICATION NO. | : 13/583879 | |
| DATED | : March 4, 2014 | |
| INVENTOR(S) | : Rekha Bansal | |

It is certified that error appears in the above-identified patent and that said Letters Patent is hereby corrected as shown below:

In the Specification

Column 1:

Please insert the following starting at line 4, column 1.

--GOVERNMENT FUNDING
This invention was made with government support under Grant No. R44AR048476 awarded by The National Institutes of Health. The United States government has certain rights to the invention.--

Signed and Sealed this
Ninth Day of June, 2015

Michelle K. Lee
*Director of the United States Patent and Trademark Office*